United States Patent
He et al.

(10) Patent No.: US 10,793,569 B2
(45) Date of Patent: *Oct. 6, 2020

(54) TOLL-LIKE RECEPTOR 7 (TLR7) AGONISTS HAVING HETEROATOM-LINKED AROMATIC MOIETIES, CONJUGATES THEREOF, AND METHODS AND USES THEREFOR

(71) Applicant: BRISTOL-MYERS SQUIBB COMPANY, Princeton, NJ (US)

(72) Inventors: Liqi He, San Jose, CA (US); Sanjeev Gangwar, Foster City, CA (US); Yam B. Poudel, Fremont, CA (US); Prasanna Sivaprakasam, Lawrenceville, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/865,009

(22) Filed: May 1, 2020

(65) Prior Publication Data

US 2020/0255429 A1    Aug. 13, 2020

Related U.S. Application Data

(63) Continuation of application No. 16/676,870, filed on Nov. 7, 2019, which is a continuation of application No. 16/103,619, filed on Aug. 14, 2018, now Pat. No. 10,508,115.

(60) Provisional application No. 62/546,222, filed on Aug. 16, 2017.

(51) Int. Cl.
| | |
|---|---|
| A61K 31/52 | (2006.01) |
| A61K 31/522 | (2006.01) |
| C07D 473/18 | (2006.01) |
| C07D 473/04 | (2006.01) |
| A61P 37/04 | (2006.01) |
| A61K 47/68 | (2017.01) |

(52) U.S. Cl.
CPC ............ C07D 473/18 (2013.01); A61P 37/04 (2018.01); A61K 47/6841 (2017.08)

(58) Field of Classification Search
CPC .... A61K 31/52; A61K 31/522; A61K 473/18; A61K 473/04
USPC .......... 514/263.34, 263.37, 263.35; 544/276, 544/272

See application file for complete search history.

(56) References Cited

U.S. PATENT DOCUMENTS

| | | | |
|---|---|---|---|
| 6,028,076 A | 2/2000 | Hirota et al. | |
| 6,376,501 B1 | 4/2002 | Isobe et al. | |
| 7,241,890 B2 | 7/2007 | Kasibhatla et al. | |
| 7,521,454 B2 | 4/2009 | Isobe et al. | |
| 7,642,350 B2 | 1/2010 | Pryde | |
| 8,148,371 B2 | 4/2012 | Isobe et al. | |
| 8,729,088 B2 | 5/2014 | Carson et al. | |
| 8,993,755 B2 | 3/2015 | Graupe et al. | |
| 9,050,376 B2 | 6/2015 | Carson et al. | |
| 9,127,006 B2 | 9/2015 | Desai et al. | |
| 9,161,934 B2 | 10/2015 | Halcomb et al. | |
| 9,173,935 B2 | 11/2015 | Maj et al. | |

(Continued)

FOREIGN PATENT DOCUMENTS

| | | |
|---|---|---|
| EP | 3381918 A1 | 10/2018 |
| WO | WO2015036044 A1 | 3/2015 |

OTHER PUBLICATIONS

Akinbobuyi et al, Synthesis of Functionalize Dpurine Analogs for Antibody Conjugation, 2015, 2015 Joint Southwestern Regional Meeting 392.

(Continued)

*Primary Examiner* — Matthew P Coughlin
*Assistant Examiner* — Sagar Patel
(74) *Attorney, Agent, or Firm* — Yuan Chao

(57) ABSTRACT

Compounds having a structure according to formula (I) or (II)

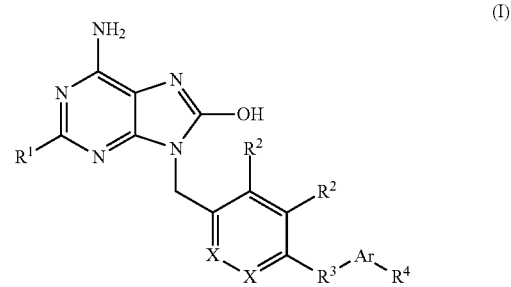

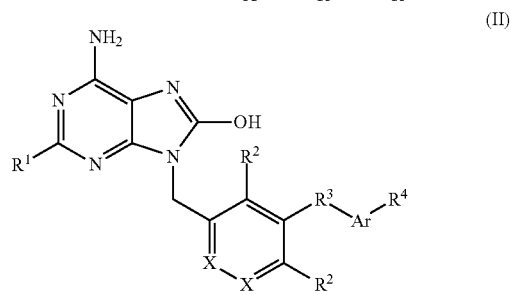

where $R^1$, $R^2$, $R^3$, $R^4$, Ar and $X^1$ are as defined herein, are agonists for the Toll-like receptor 7 (TLR7) and can be used as adjuvants for stimulating the immune system. Some such compounds can be used in conjugates for targeted delivery to the organ or tissue of intended action.

1 Claim, 7 Drawing Sheets

(56) References Cited

U.S. PATENT DOCUMENTS

| | | |
|---|---|---|
| 9,295,732 B2 | 3/2016 | Lioux et al. |
| 9,902,730 B2 | 2/2018 | Li et al. |
| 2007/0225303 A1 | 9/2007 | Ogita et al. |
| 2009/0105212 A1 | 4/2009 | Isobe et al. |
| 2009/0118263 A1 | 5/2009 | Hashimoto et al. |
| 2010/0093998 A1* | 4/2010 | Isobe .............. A61P 27/14 540/575 |
| 2011/0028715 A1 | 2/2011 | Isobe et al. |
| 2012/0003298 A1 | 1/2012 | Barberis et al. |
| 2012/0083473 A1 | 4/2012 | Holldack et al. |
| 2012/0231023 A1 | 9/2012 | Zurawski et al. |
| 2013/0202629 A1 | 8/2013 | Carson et al. |
| 2014/0141033 A1 | 5/2014 | Vernejoul et al. |
| 2014/0323441 A1 | 10/2014 | Bonfanti et al. |
| 2016/0199499 A1 | 7/2016 | Carson et al. |
| 2017/0044168 A1 | 2/2017 | Cortez et al. |
| 2017/0121421 A1 | 5/2017 | Cortez et al. |
| 2017/0273983 A1 | 9/2017 | Tianqing et al. |
| 2018/0148452 A1 | 5/2018 | Ding et al. |

OTHER PUBLICATIONS

Akinbobuyi et al., Facile syntheses of functionalized toll-like receptor 7 agonists, 2015, 459-460, 56, Tetrahedron Letters.

Akinbobuyi et al., Synthesis and evaluation of purine-based Toll-like, 2013, Abstracts, 69th Southwest Regional Meeting.

Akinbobuyi et al., Synthesis and immunostimulatory activity of substituted TLR7 agonists, 2016, 4246-4249, 26, Bioorganic & Medicinal Chemistry Letters.

Beesu et al., Identification of High-Potency Human TLR8 and Dual TLR7/TLR8 Agonists in Pyrimidine-2,4-diamines, 2017, 2084-2098, 60, J Med Chem.

Berghofer et al., Natural and Synthetic TLR7 Ligands Inhibit CpG-A- and CpG-C-Oligodeoxynucleotide-Induced IFN . . . , 2007, 4072-4079, 178, The Journal of Immunology.

Chan et al., Synthesis and Characterization of PEGylated Toll Like Receptor 7 Ligands, 2011, 445-454, 22, Bioconjugate Chemistry.

Chan et al., Synthesis and Immunological Characterization of Toll-Like Receptor 7 Agonistic Conjugates, 2009, 1194-_1200, vol. 20, Bioconjugate Chemistry.

Gadd et al., Targeted Activation of Toll-Like Receptors: Conjugation of a Toll-Like Receptor 7 Agonist to a Monoclonal Antibody Maintains Antigen Binding and Specificity, 2015, 1743_1752, 26, Bioconjugate Chemistry.

ISA_EP, International Search Report, dated Nov. 26, 2018.

Isobe et al., Synthesis and Biological Evaluation of Novel 9-Substituted-8-Hydroxyadenine Derivatives as Potent Interferon Inducers, 2006, 2088-2095, 49, J Med Chem.

Koga-Yamakawa et al., Intratracheal and oral administration of SM-276001: A selective TLR7 agonist, leads to antitumor efficacy in primary and metastatic models of cancer, 2013, 580-590, 132, IJC Cancer.

Lund et al., Recognition of single-stranded RNA viruses by Toll-like receptor 7, 2004, 5598-5603, 101:15, ProcNatlAcadSciUSA.

McGowan et al., Identification and Optimization of Pyrrolo[3,2-d]pyrimidine Toll-like Receptor 7 (TLR7) Selective Agonists for the Treatment of Hepatitis B, 2017, 6137-6151, 60, J Med Chem.

Musmuca et al., Small-Molecule Interferon Inducers. Toward the Comprehension of the Molecular Determinants through Ligand-Based Approaches, 2009, 1777-1786, 49, J Chem Inform Model.

Nakamira et al., Synthesis and evaluation of 8-oxoadenine derivatives as potent Toll-like receptor 7 agonists with high water solubility, 2013, 669-672, 23, BioorgMedChemLett.

Rachel Peterson, Synthesis of Sulfur and Amino 8-Substituted Adenine Derivatives as TLR7 Agonists, 2014, 1-37.

Roethle, Identification and Optimization of Pteridinone Toll-like Receptor 7 (TLR7) Agonists for the Oral Treatment of Viral Hepatitis, 2013, 7324-7333, 56, J Med Chem.

Yoshiaki, JP2004137157_abst, 2004.

Yu et al., Toll-Like Receptor 7 Agonists: Chemical Feature Based Pharmacophore Identification and Molecular Docking Studies, 2013, 1-12, Plossone.

Zacharie J. Seifert, Synthesis and Evaluation of 8-Substituted Adenine Derivatives as Toll-like Receptor 7 Agonists, 2015, 1-60.

Hang et al., Structural Analysis Reveals that Toll-like Receptor 7 Is a Dual Receptor for Guanosine and Single-Stranded RNA, 2016, 737_748, 45, Immunity.

* cited by examiner

TOLL-LIKE RECEPTOR 7 (TLR7) AGONISTS HAVING HETEROATOM-LINKED AROMATIC MOIETIES, CONJUGATES THEREOF, AND METHODS AND USES THEREFOR

CROSS-REFERENCE TO RELATED APPLICATIONS

This application is a continuation of allowed U.S. application Ser. No. 16/676,870, filed Nov. 7, 2019; which is a continuation of U.S. application Ser. No. 16/103,619, filed Aug. 14, 2018, now U.S. Pat. No. 10,508,115; which claims the benefit under 35 U.S.C. § 119(e) of U.S. Provisional Application Ser. No. 62/546,222, filed Aug. 16, 2017; the disclosures of which are incorporated herein by reference.

BACKGROUND OF THE INVENTION

This disclosure relates to Toll-like receptor 7 ("TLR7") agonists and conjugates thereof, and methods for the preparation and use of such agonists and their conjugates.

Toll-like receptors ("TLRs") are cell-surface receptors that recognize pathogen-associated molecular patterns ("PAMPs"). Activation of a TLR by the binding of a corresponding PAMP signals potential infection by a pathogen and stimulates the immune system to fight the infection. Humans have 11 TLRs, named TLR1 through TLR11.

The activation of a TLR—with TLR7 being the most studied—by an agonist can have an adjuvant effect on the action of vaccines and immunotherapy agents in treating a variety of conditions other than actual pathogen infection, by stimulating the immune response.

TLR7 recognizes PAMPs associated with single-stranded RNA viruses. Its activation induces secretion of Type I interferons such as IFNα and IFNβ (Lund et al. 2004). It has two binding sites, one for single stranded RNA ligands such as ssRNA40 (Berghöfer et al. 2007) and one for guanosine (Zhang et al. 2016).

TLR7 can bind to, and be activated by, guanosine-like synthetic agonists such as imiquimod, resiquimod, and gardiquimod, which are based on a 1H-imidazo[4,5-c]quinoline scaffold.

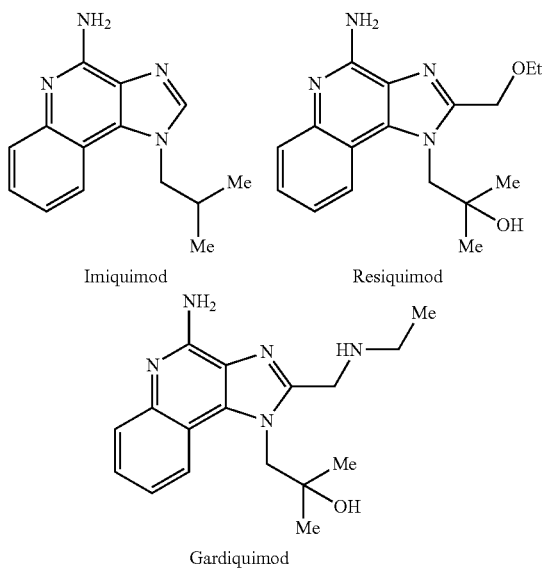

Imiquimod

Resiquimod

Gardiquimod

Synthetic TLR7 agonists based on a pteridinone molecular scaffold are also known, as exemplified by vesatolimod (Desai et al. 2015), which has been in Phase 2 clinical trials. The potency of vesatolimod is reported to be 100× less than that of the corresponding purine-8-one compound, as measured by IFN-α induction (Roethle et al. 2013).

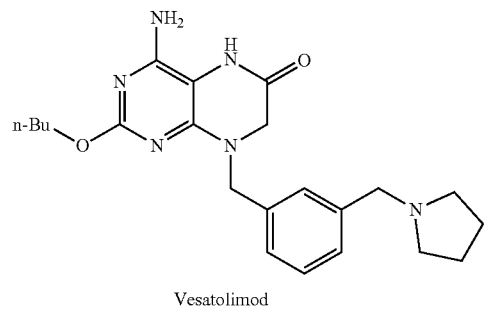

Vesatolimod

Other synthetic TLR7 agonists are based on a purine-like scaffold, frequently according to formula (A):

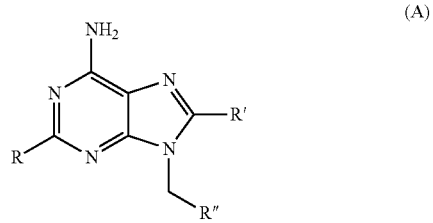

(A)

where R, R', and R" are structural variables, with R" typically containing an unsubstituted or substituted aromatic or heteroaromatic ring.

Disclosures of bioactive molecules having a purine-like and their uses in treating conditions such as fibrosis, inflammatory disorders, cancer, or pathogenic infections include: Akinbobuyi et al. 2015b and 2016; Barberis et al. 2012; Carson et al. 2014; Ding et al. 2016, 2017a, and 2017b; Graupe et al. 2015; Hashimoto et al. 2009; Holldack et al. 2012; Isobe et al. 2009a and 2012; Jin et al. 2017a and 2017b; Peterson 2014; Pryde 2010; and Seifert 2015.

The group R" can be pyridyl: Bonfanti et al. 2015a and 2015b; Halcomb et al. 2015; Hirota et al. 2000; Isobe et al. 2000, 2002, 2004, 2006, 2009a, 2011, and 2012; Kasibhatla et al. 2007; Koga-Yamakawa et al. 2013; Musmuca et al. 2009; Nakamura 2012; Ogita et al. 2007; and Yu et al. 2013.

Bonfanti et al. 2015b discloses TLR7 modulators in which the two rings of a purine moiety are spanned by a macrocycle:

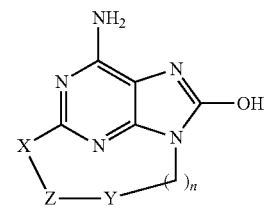

A TLR7 agonist can be conjugated to a partner molecule, which can be, for example, a phospholipid, a poly(ethylene glycol) ("PEG"), or another TLR (commonly TLR2). Exemplary disclosures include: Carson et al. 2013, 2015, and 2016, Chan et al. 2009 and 2011, Lioux et al. 2016, Maj et al. 2015, Ban et al. 2017; Vernejoul et al. 2014, and Zurawski et al. 2012. Conjugation to an antibody has also been disclosed: Akinbobuyi et al. 2013 and 2015a, and Gadd et al. 2015. A frequent conjugation site is at the R" group of formula (A).

TLR7 agonists based on a 5H-pyrrolo[3,2-d]pyrimidine scaffold have also been disclosed. See Cortez et al. 2017a and 2017b, McGowan et al. 2017, and Li et al. 2018.

Jensen et al. 2015 discloses the use of cationic lipid vehicles for the delivery of TLR7 agonists.

Some TLR7 agonists, including resiquimod are dual TLR7/TLR8 agonists. See, for example, Beesu et al. 2017; Lioux et al. 2016; and Vernejoul et al. 2014.

TLR7 agonists based on a 5H-pyrrolo[3,2-d]pyrimidine scaffold have also been disclosed. See Cortez et al. 2017a and 2017b, McGowan et al. 2017, and Li et al. 2018.

Full citations for the documents cited herein by first author or inventor and year are listed at the end of this specification.

BRIEF SUMMARY OF THE INVENTION

In one aspect, this specification provides a compound having a structure according to formula (I) or (II)

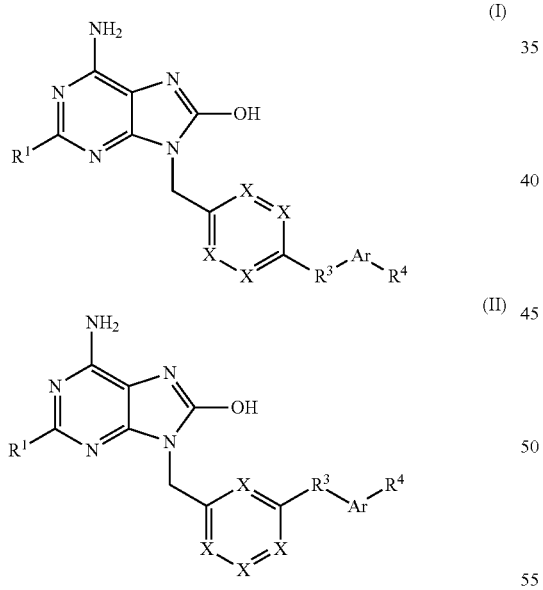

wherein $R^1$ is $(C_1$-$C_5$ alkyl)O, $(C_1$-$C_2$ alkyl)O$(CH_2)_{2\text{-}30}$, $(C_1$-$C_5$ alkyl)C(=O)O, $(C_1$-$C_5$ alkyl)NH, $(C_1$-$C_2$ alkyl)O$(CH_2)_{2\text{-}3}$NH, or $(C_1$-$C_5$ alkyl)C(=O)NH;

X is, independently for each occurrence thereof, $CR^2$ or N;

$R^2$ is, independently for each occurrence thereof, H, $C_1$-$C_3$ alkyl, halo, O($C_1$-$C_3$ alkyl), CN, or $NO_2$;

$R^3$ is O, S, NH, or N($C_1$-$C_3$ alkyl);

Ar is

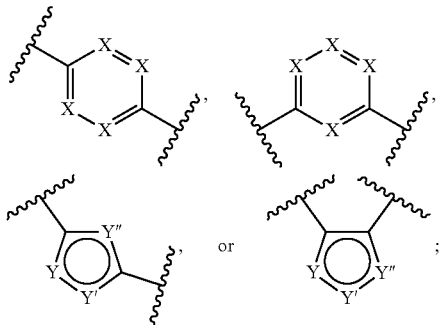

where one of Y, Y' and Y" is selected from —O—, —S—, —NH— and —N($C_1$-$C_3$ and the other two of Y, Y', and Y" are selected from =N— and =CR—;

$R^4$ is H, $C_1$-$C_3$ alkyl, halo, O($C_1$-$C_3$ alkyl), CN, $NO_2$, or $(CH_2)_xR^5$, where the subscript x is 1, 2, 3, or 4; and $R^5$ is halo, OH, CN, $NH_2$, NH($C_1$-$C_5$ alkyl), N($C_1$-$C_5$ alkyl)$_2$, NH($C_3$-$C_6$ cycloalkyl), NH($C_4$-$C_8$ bicycloalkyl), NH($C_6$-$C_{10}$ spirocycloalkyl), N($C_3$-$C_6$ cycloalkyl)$_2$, NH($CH_2$)$_{1\text{-}3}$(aryl), N(($CH_2$)$_{1\text{-}3}$(aryl))$_2$, a cyclic amine moiety having the structure

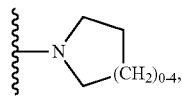

a 6-membered aromatic or heteroaromatic moiety or a 5-membered heteroaromatic moiety;

wherein an alkyl, cycloalkyl, bicycloalkyl, spirocycloalkyl, cyclic amine, 6-membered aromatic or heteroaromatic, or 5-membered heteroaromatic moiety is optionally substituted with one or more substituents selected from OH, halo, CN, ($C_1$-$C_3$ alkyl), O($C_1$-$C_3$ alkyl), C(=O)($C_1$-$C_3$ alkyl), $SO_2$($C_1$-$C_3$ alkyl), $CO_2$ ($C_1$-$C_3$ alkyl), $NH_2$, NH(Me), N(Me)$_2$, NH(Et), N(Et)$_2$, and N($C_1$-$C_3$ alkyl)$_2$; and a cycloalkyl, bicycloalkyl, spirocycloalkyl, or cyclic amine moiety may have a $CH_2$ group replaced by O, S, NH, N($C_1$-$C_3$ alkyl), or N(Boc).

Compounds according to formula (I) and (II) have activity as TLR7 agonists and some of them can be conjugated for targeted delivery to a target tissue or organ of intended action.

BRIEF DESCRIPTION OF THE DRAWING(S)

DETAILED DESCRIPTION OF THE INVENTION

Definitions

Figure 1:
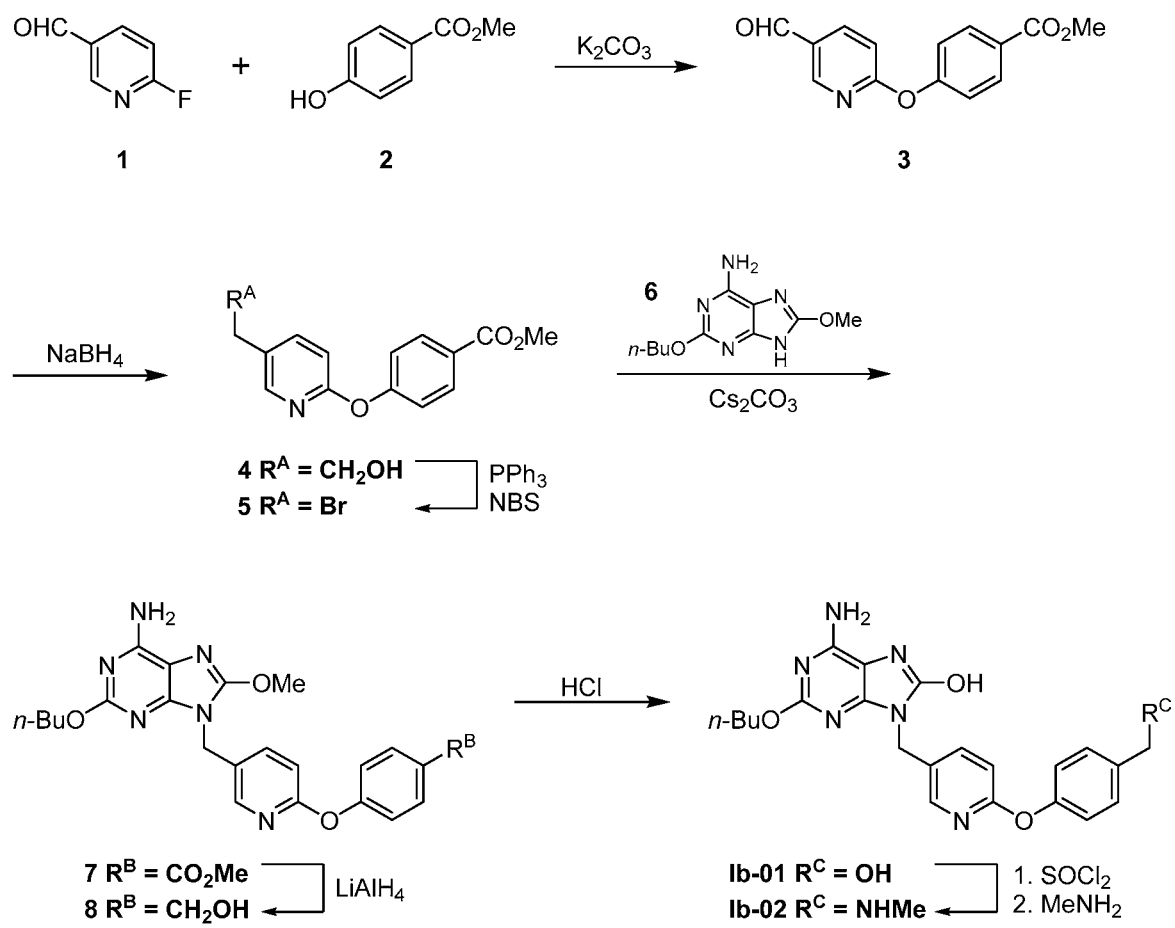
FIG. 1, FIG. 2, FIG. 3 and FIG. 7 show schemes for preparing compounds of this disclosure.

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, Cm, $CH_2$ and $CH_3$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and Cm domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the $F_V$ fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain $F_V$, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

Unless indicated otherwise—for example by reference to the linear numbering in a SEQ ID NO: listing—references to the numbering of amino acid positions in an antibody heavy or light chain variable region ($V_H$ or $V_L$) are according to the Kabat system (Kabat et al., "Sequences of proteins of immunological interest, 5th ed., Pub. No. 91-3242, U.S. Dept. Health & Human Services, NIH, Bethesda, Md., 1991, hereinafter "Kabat") and references to the numbering of amino acid positions in an antibody heavy or light chain constant region ($C_{H1}$, $C_{H2}$, $CH_3$, or $C_L$) are according to the EU index as set forth in Kabat. See Lazar et al., US 2008/0248028 A1, the disclosure of which is incorporated herein by reference, for examples of such usage. Further, the ImMunoGeneTics Information System (IMGT) provides at its website a table entitled "IMGT Scientific Chart: Correspondence between C Numberings" showing the correspondence between its numbering system, EU numbering, and Kabat numbering for the heavy chain constant region.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.+

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpy-ridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO₂H, —C(=O)NHOH, —C(=O)O(alkyl), —C(=O)O(hydroxyalkyl), —C(=O)NH₂, —C(=O)NH(alkyl), —C(=O)N(alkyl)₂, —OC(=O)(alkyl), —OC(=O)(hydroxyalkyl), —OC(=O)O(alkyl), —OC(=O)O(hydroxyalkyl), —OC(=O)NH₂, —OC(=O)NH(alkyl), —OC(=O)N(alkyl)₂, azido, —NH₂, —NH(alkyl), —N(alkyl)₂, —NH(aryl), —NH(hydroxyalkyl), —NHC(=O)(alkyl), —NHC(=O)H, —NHC(=O)NH₂, —NHC(=O)NH(alkyl), —NHC(=O)N(alkyl)₂, —NHC(=NH)NH₂, —OSO₂(alkyl), —SH, —S(alkyl), —S(aryl), —S(cycloalkyl), —S(=O)alkyl, —SO₂(alkyl), —SO₂NH₂, —SO₂NH(alkyl), —SO₂N(alkyl)₂, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO₂H, —C(=O)NHOH, —C(=O)O(alkyl), —C(=O)O(hydroxyalkyl), —C(=O)NH₂, —C(=O)NH(alkyl), —C(=O)N(alkyl)₂, —OC(=O)(alkyl), —OC(=O)(hydroxyalkyl), —OC(=O)O(alkyl), —OC(=O)O(hydroxyalkyl), —OC(=O)NH₂, —OC(=O)NH(alkyl), —OC(=O)N(alkyl)₂, azido, —NH₂, —NH(alkyl), —N(alkyl)₂, —NH(aryl), —NH(hydroxyalkyl), —NHC(=O)(alkyl), —NHC(=O)H, —NHC(=O)NH₂, —NHC(=O)NH(alkyl), —NHC(=O)N(alkyl)₂, —NHC(=NH)NH₂, —OSO₂(alkyl), —SH, —S(alkyl), —S(aryl), —S(=O)alkyl, —S(cycloalkyl), —SO₂(alkyl), —SO₂NH₂, —SO₂NH(alkyl), and —SO₂N(alkyl)₂. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH₂, —OC(=O)NH(alkyl), —OC(=O)N(alkyl)₂, azido, —NH₂, —NH(alkyl), —N(alkyl)₂, —NH(aryl), —NHC(=O)(alkyl), —NHC(=O)H, —NHC(=O)NH₂, —NHC(=O)NH(alkyl), —NHC(=O)N(alkyl)₂, and —NHC(=NH)NH₂. Especially preferred are phenyl, cyano, halo, hydroxyl, nitro, C₁-C₄alkyoxy, O(C₂-C₄ alkylene)OH, and O(C₂-C₄ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —S(=O)(alkyl), —C(=O)H, —CO₂H, —C(=O)NHOH, —C(=O)O(alkyl), —C(=O)O(hydroxyalkyl), —C(=O)NH₂, —C(=O)NH(alkyl), —C(=O)N(alkyl)₂, —OC(=O)(alkyl), —OC(=O)(hydroxyalkyl), —OC(=O)O(alkyl), —OC(=O)O(hydroxyalkyl), —OC(=O)NH₂, —OC(=O)NH(alkyl), —OC(=O)N(alkyl)₂, azido, —NH₂, —NH(alkyl), —N(alkyl)₂, —NH(aryl), —NH(hydroxyalkyl), —NHC(=O)(alkyl), —NHC(=O)H, —NHC(=O)NH₂, —NHC(=O)NH(alkyl), —NHC(=O)N(alkyl)₂, —NHC(=NH)NH₂, —OSO₂(alkyl), —SH, —S(alkyl), —S(aryl), —S(cycloalkyl), —S(=O)alkyl, —SO₂(alkyl), —SO₂NH₂, —SO₂NH(alkyl), and —SO₂N(alkyl)₂. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO₂H, —C(=O)NHOH, —C(=O)O(alkyl), —C(=O)O(hydroxyalkyl), —C(=O)NH₂, —C(=O)NH(alkyl), —C(=O)N(alkyl)₂, —OC(=O)(alkyl), —OC(=O)(hydroxyalkyl), —OC(=O)O(alkyl), —OC(=O)O(hydroxyalkyl), —OC(=O)NH₂, —OC(=O)NH(alkyl), —OC(=O)N(alkyl)₂, —NH₂, —NH(alkyl), —N(alkyl)₂, —NH(aryl), —NHC(=O)(alkyl), —NHC(=O)H, —NHC(=O)NH₂, —NHC(=O)NH(alkyl), —NHC(=O)N(alkyl)₂, and —NHC(=NH)NH₂. Especially preferred are C₁-C₄ alkyl, cyano, nitro, halo, and C₁-C₄alkoxy.

Where a range is stated, as in "C₁-C₅ alkyl" or "5 to 10%," such range includes the end points of the range, as in C₁ and C₅ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C₁-C₅ alkyl, C₂-C₅ alkenyl or C₂-C₅ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line (—) transverse to a bond or an asterisk (*) at the end of the bond denotes a covalent attachment site. For instance, a statement that R is

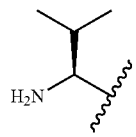

or that R

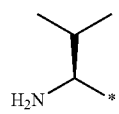

is in the formula

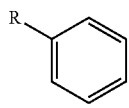

means

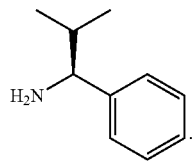

In the formulae of this specification, a bond traversing an aromatic ring between two carbons thereof means that the group attached to the bond may be located at any of the positions of the aromatic ring made available by removal of the hydrogen that is implicitly there. By way of illustration, the formula

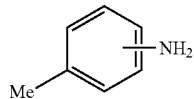

represents

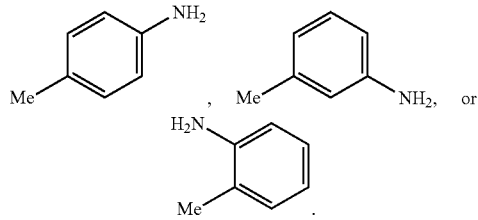

In another illustration,

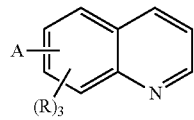

represents

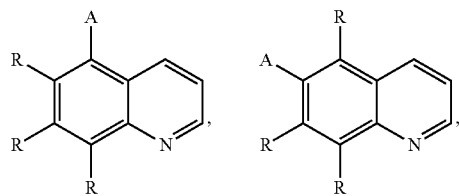

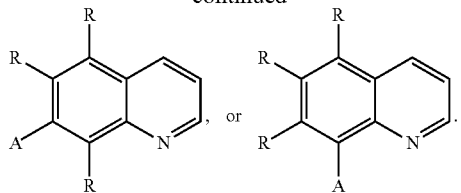

Generally, tautomeric structures have been rendered herein in the enol form, as a matter of consistency and convenience.

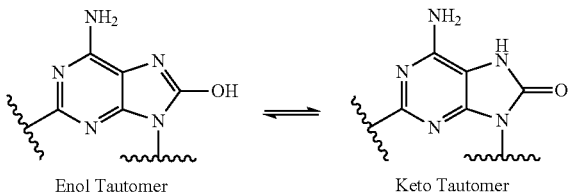 [SMILES: *c1nc(N)c2nc(O)n(*)c2n1 ; *c1nc(N)c2[nH]c(=O)n(*)c2n1]

Those skilled in the art will appreciate that they could also have be rendered in the equivalent keto form and that the two tautomers equivalent.

Compounds $R^1$ in formulae (I) and (II) preferably is n-BuO, n-BuNH, EtO, MeO, or MeOCH$_2$CH$_2$O; more preferably n-BuO or MeOCH$_2$CH$_2$O; and most preferably n-BuO.

In formulae (I) and (II), preferably each IV is H.

In formulae (I) and (II), preferably $R^3$ is O.

In one embodiment, a compound according to formula (I) is represented by formula (I'), wherein each X' is independently CH or N and $R^1$, Ar, and $R^4$ are as defined above in respect of formulae (I)/(II):

(I')

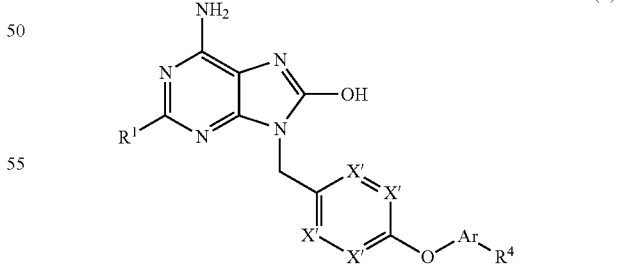

In one embodiment, a compound according to formula (II) is represented by formula (II'), wherein each X' is independently CH or N and $R^1$, Ar, and $R^4$ are as defined above in respect of formulae (I)/(II):

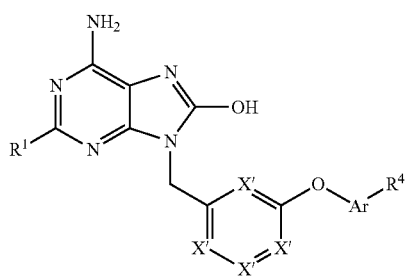

(II')

In one embodiment, a compound according to formula (I) is represented by formula (Ia), where x, $R^1$ and $R^5$ are as defined above in respect of formulae (I)/(II):

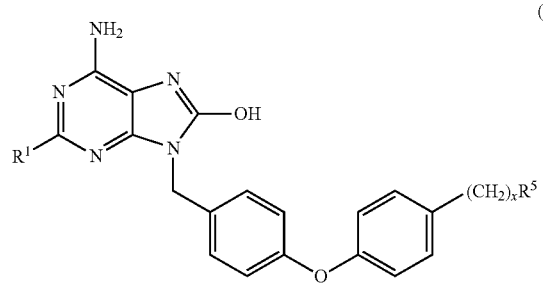

(Ia)

In one embodiment, a compound according to formula (I) is represented by formula (Ib), where x, $R^1$ and $R^5$ are as defined above in respect of formulae (I)/(II):

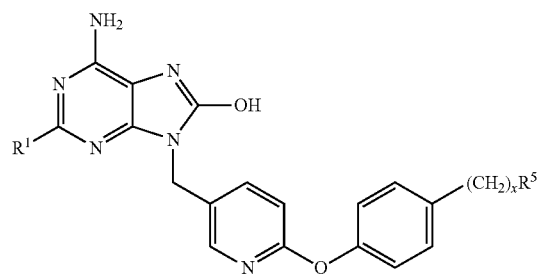

(Ib)

In one embodiment, a compound according to formula (I) is represented by formula (Ic), where x, $R^1$ and $R^5$ are as defined above in respect of formulae (I)/(II):

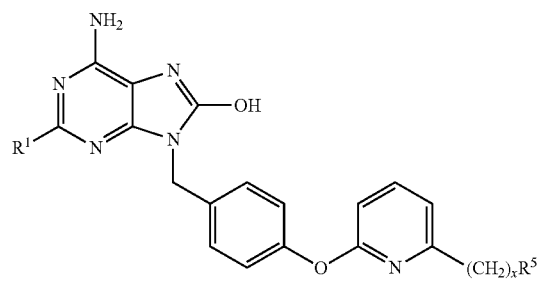

(Ic)

In one embodiment, a compound according to formula (I) is represented by formula (Id), where x, $R^1$ and $R^5$ are as defined above in respect of formulae (I)/(II):

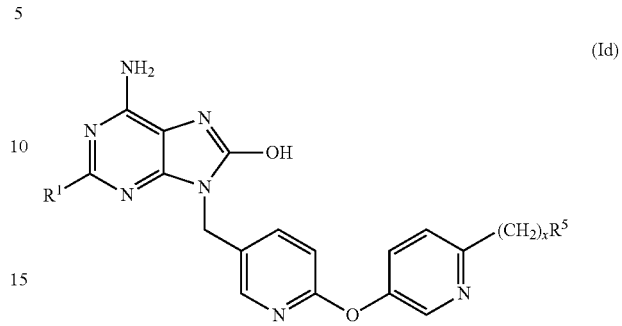

(Id)

In one embodiment, a compound according to formula (I) is represented by formula (Ie), where x, $R^1$ and $R^5$ are as defined above in respect of formulae (I)/(II):

(Ie)

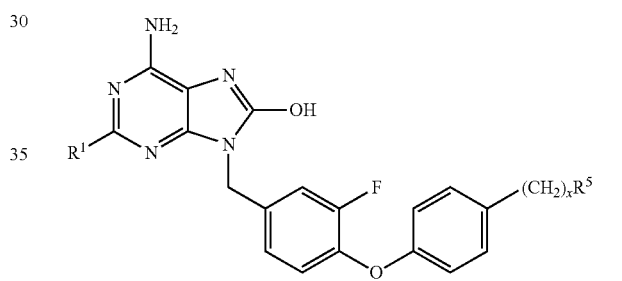

In one embodiment, a compound according to formula (I) is represented by formula (If), where x, $R^1$ and $R^5$ are as defined above in respect of formulae (I)/(II):

(If)

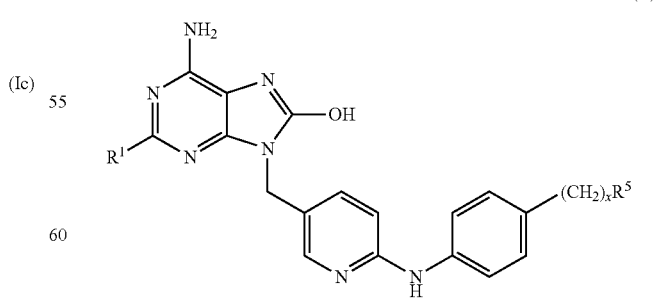

In one embodiment, a compound according to formula (I) is represented by formula (Ig), where x, $R^1$ and $R^5$ are as defined above in respect of formulae (I)/(II):

(Ig)

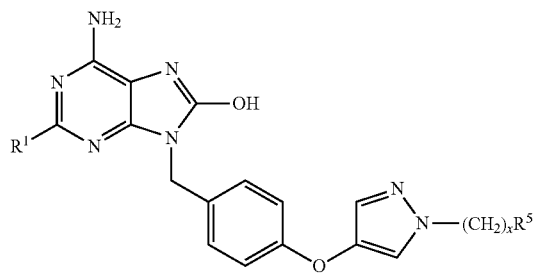

In one embodiment, a compound according to formula (II) is represented by formula (IIa), where x, $R^1$ and $R^5$ are as defined above in respect of formulae (I)/(II):

(IIa)

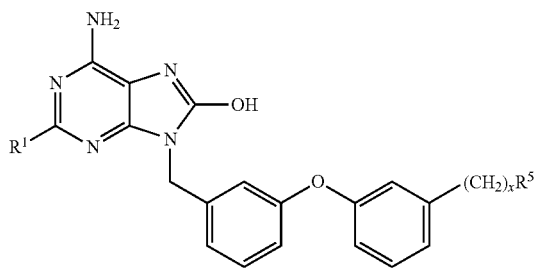

In formulae (Ia), (Ib), (Ic), (Id), (Ie), (If), and (IIa), preferably $R^1$ is n-BuO and the subscript x is 1.

In formulae (I), (I'), (II), (II'), (Ia), (Ib), (Ic), (Id), (Ie), (If), and (IIa) (in the first four formulae in the instance where $R^4$ is $(CH_2)_xR^5$ with x preferably being 1), $R^5$ preferably is OH, Cl,

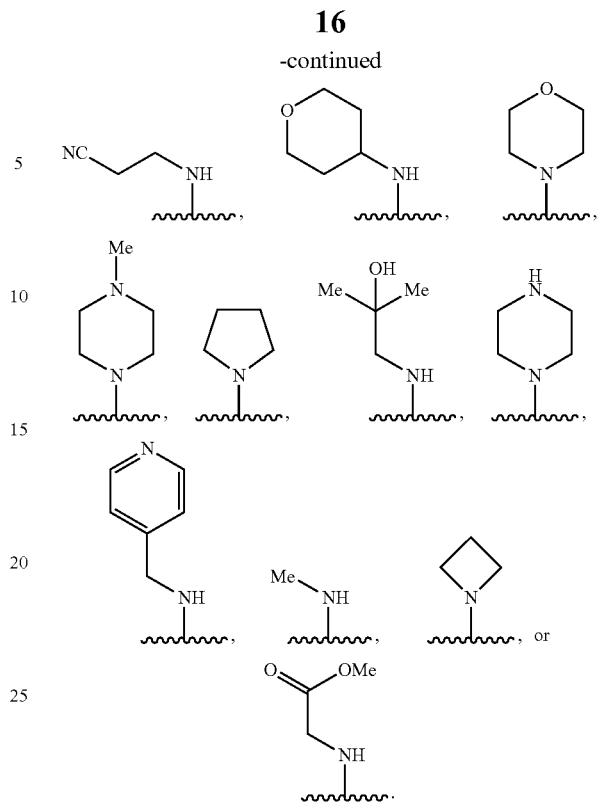

Preferably, in formulae (I) and (II), no more than two X's, and more preferably no more than one X, in any given aromatic ring is N.

Preferably, in formulae (I'), (II'), (Ia), (Ib), (IIa), and (IId), no more than two X's, and more preferably no more than one X, in any given aromatic ring is N.

Examples of compounds according to formula (Ia) include:

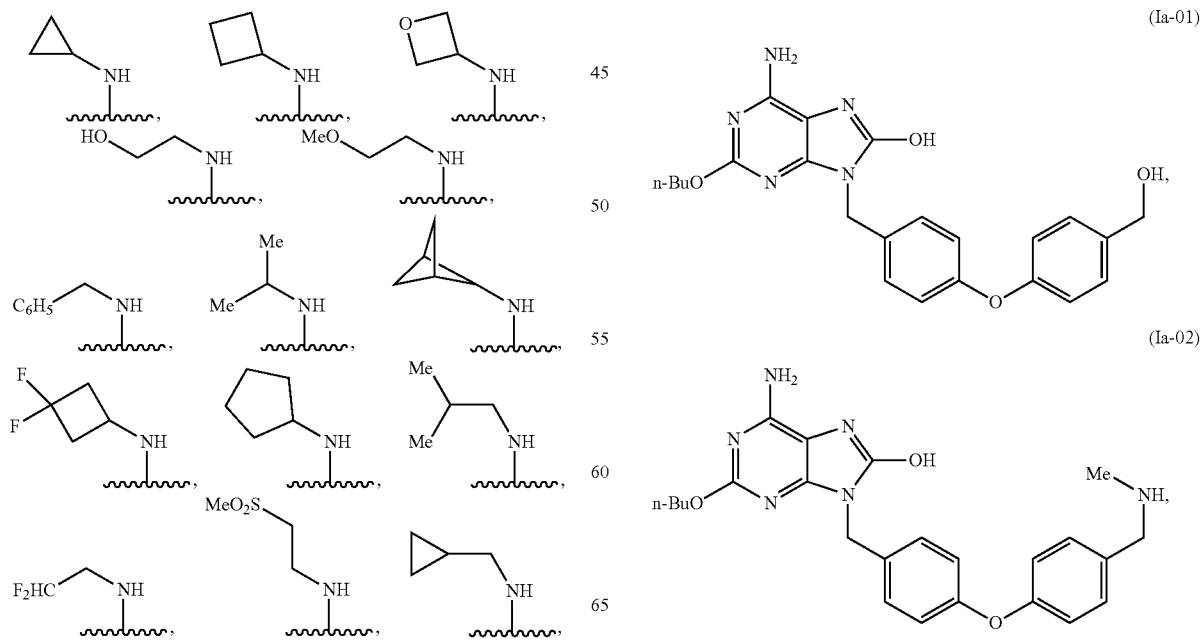

-continued
(Ia-03)
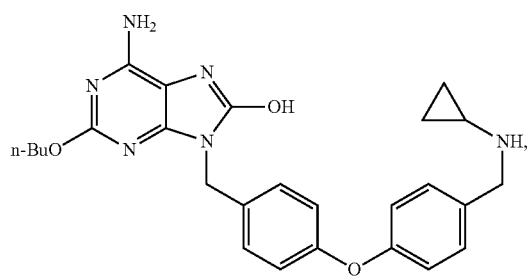
(Ia-04)
(Ia-05)
(Ia-06)
(Ia-07)
and
-continued
(Ia-08)
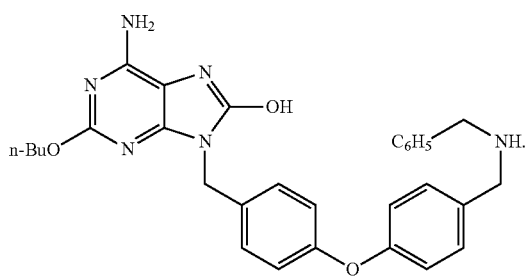
Examples of compounds according to formula (Ib) include:
(Ib-01)
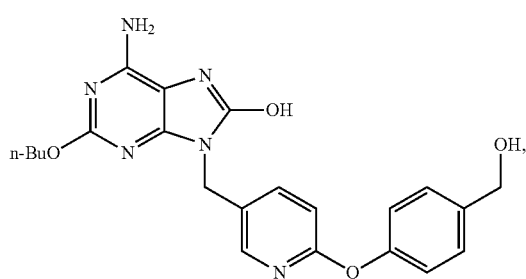
(Ib-02)
(Ib-03)
(Ib-04)
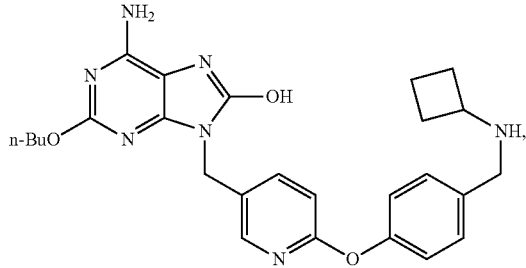

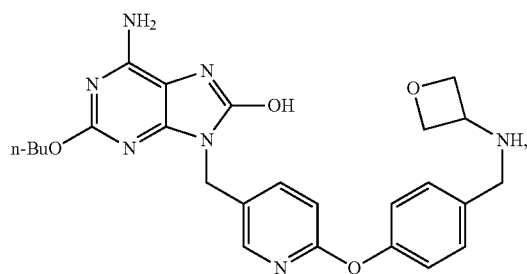
(Ib-05)
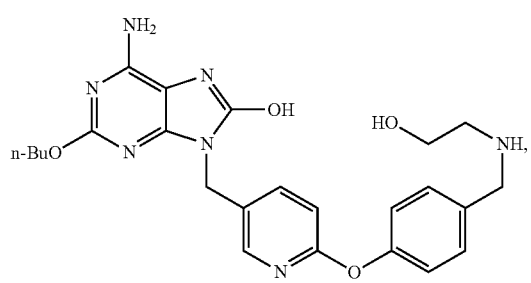
(Ib-06)
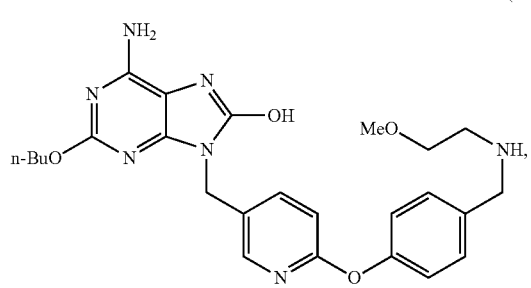
(Ib-07)
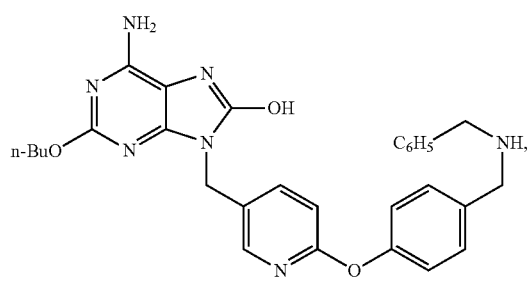
(Ib-08)
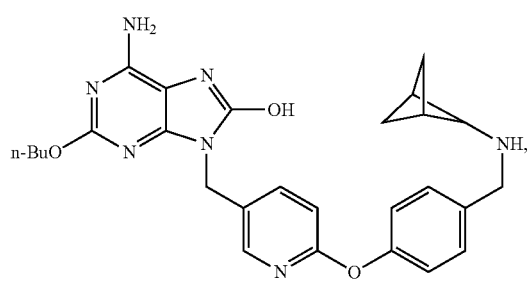
(Ib-09)
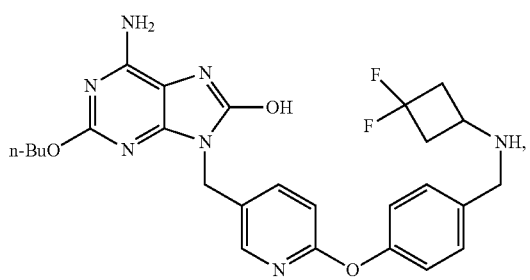
(Ib-10)
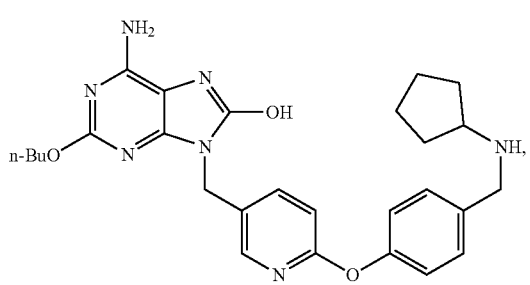
(Ib-11)
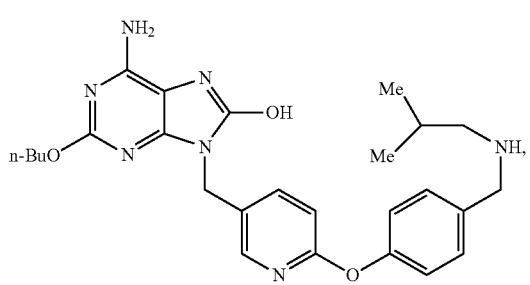
(Ib-12)
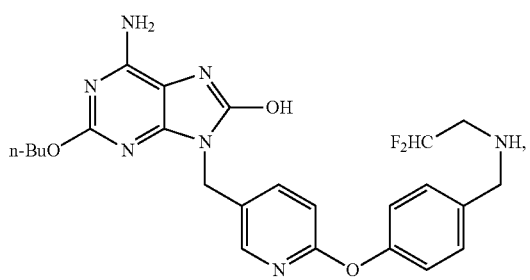
(Ib-13)
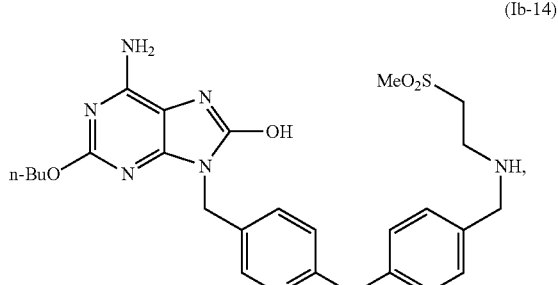
(Ib-14)

(Ib-15)
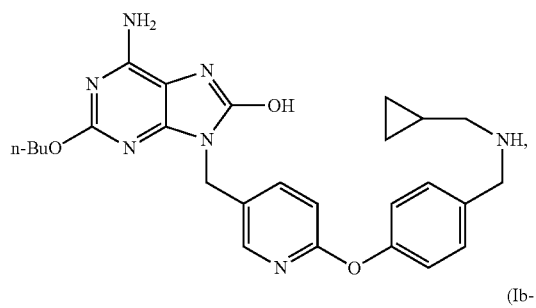
(Ib-16)
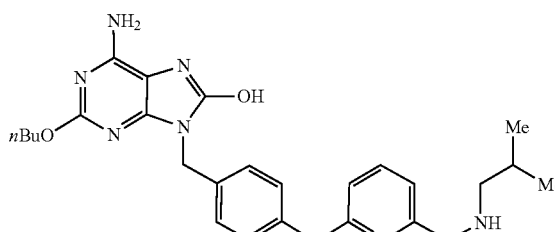
and
(Ib-17)
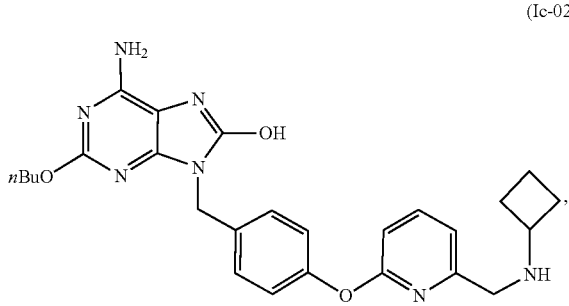
Examples of compounds according to formula (Ic) include:
(Ic-01)
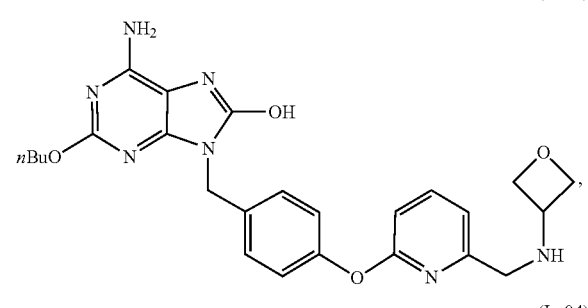
(Ic-02)
(Ic-03)
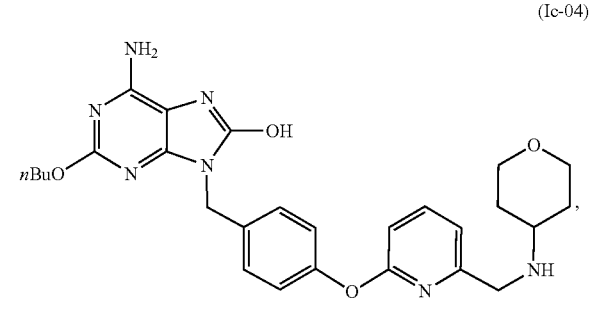
(Ic-04)
(Ic-05)
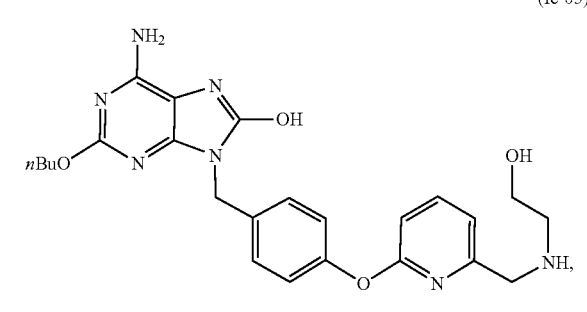
(Ic-06)
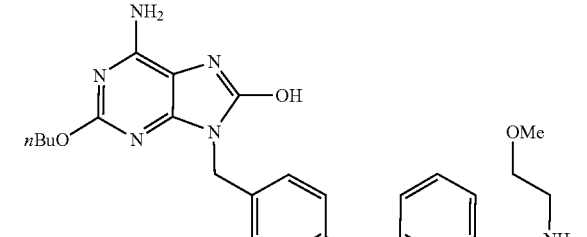
(Ic-07)
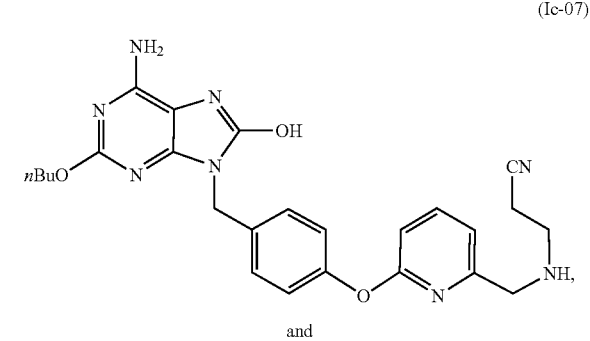
and (Ic-08)
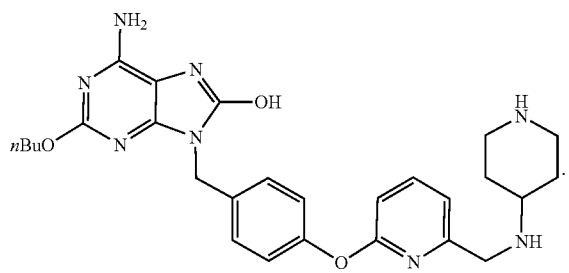
Examples of compounds according to formula (Id) include:
(Id-01)
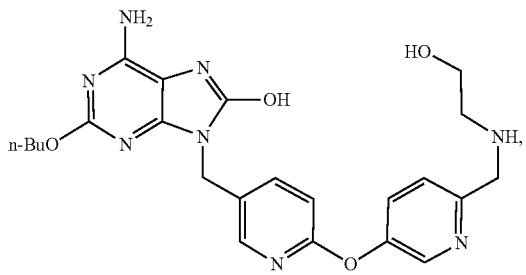
(Id-02)
(Id-03)
(Id-04)
(Id-05)
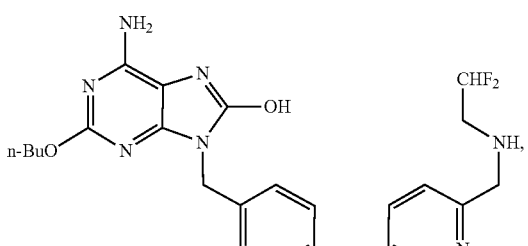
(Id-06)
(Id-07)
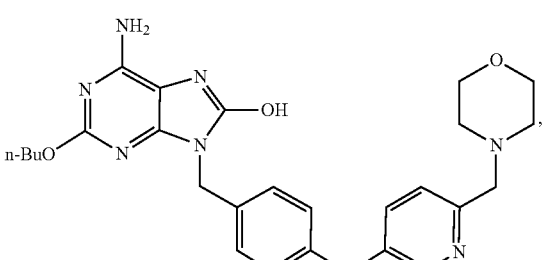
(Id-08)
and
(Id-09)
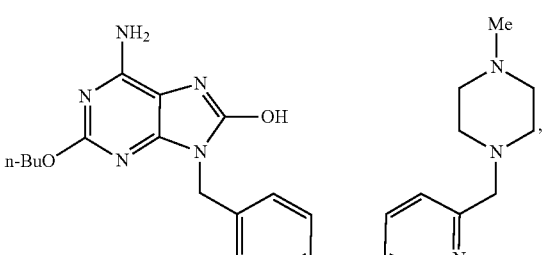
Examples of compounds according to formula (Ie) include:

(Ie-01)
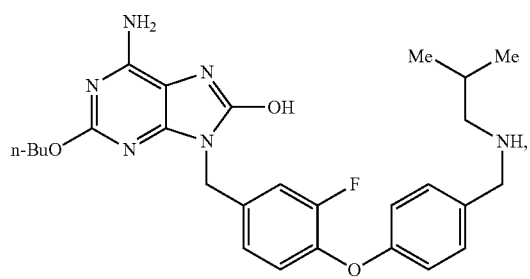
(Ie-02)
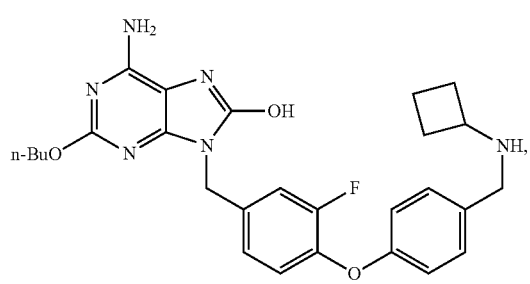
(Ie-03)
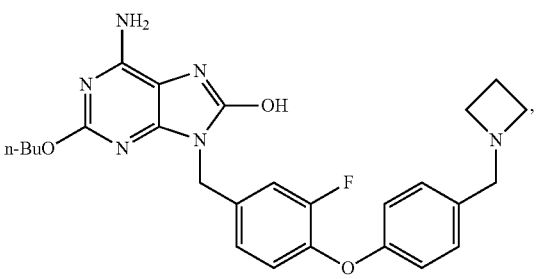
(Ie-04)
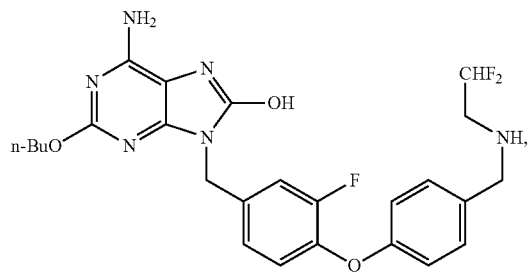
(Ie-05)
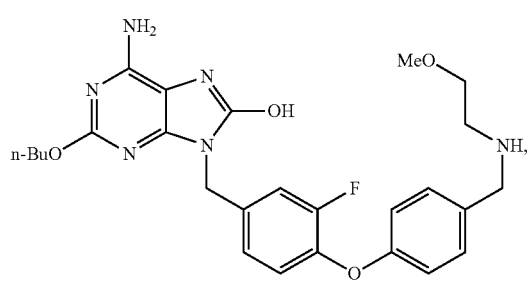
(Ie-06)
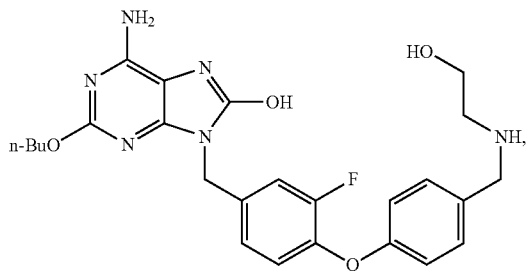
(Ie-07)
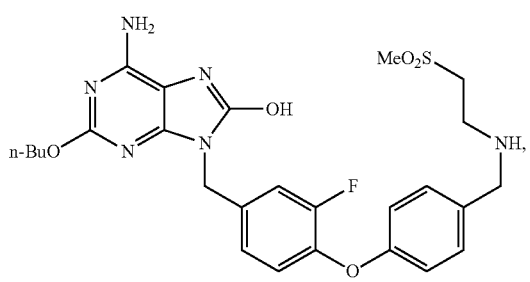
(Ie-08)
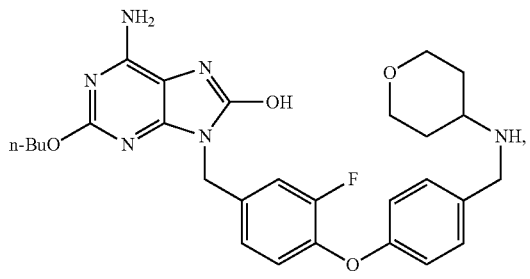
(Ie-09)
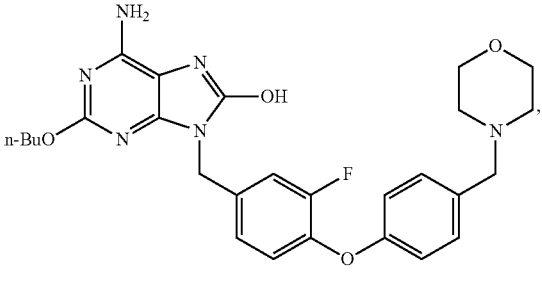
and
(Ie-10)
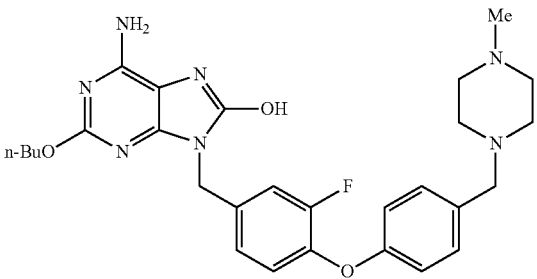
Examples of compounds according to formula (If) include:

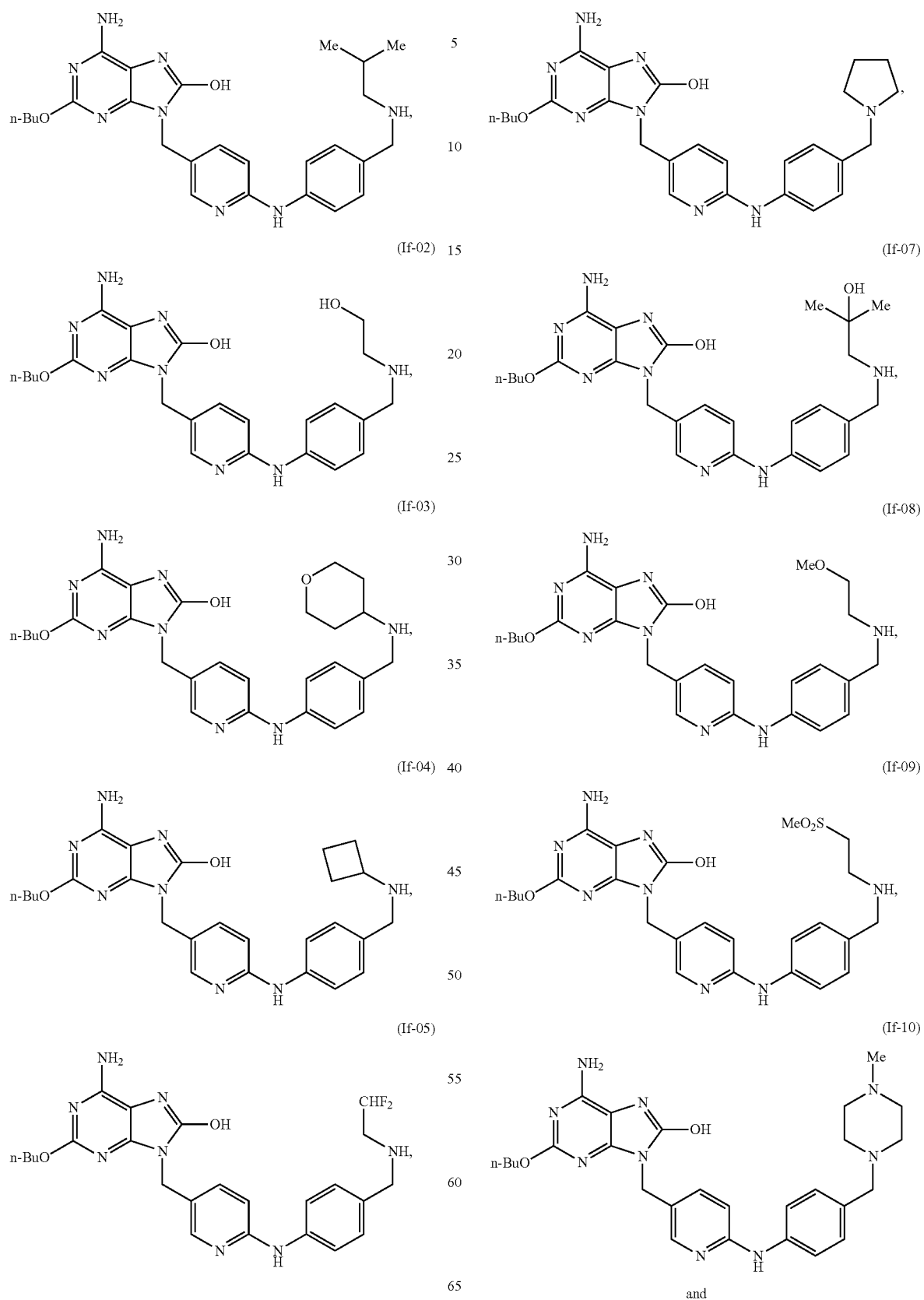

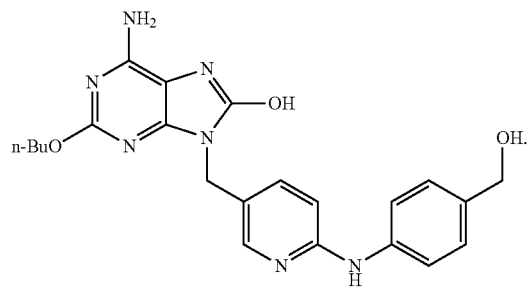
(If-11)
An example of a compound according to formula (Ig) is:
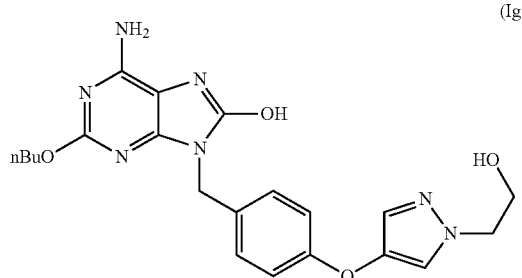
(Ig-01)
Examples of compounds according to formula (IIa) include:
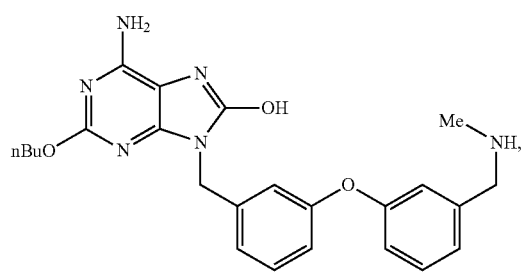
(IIa-01)
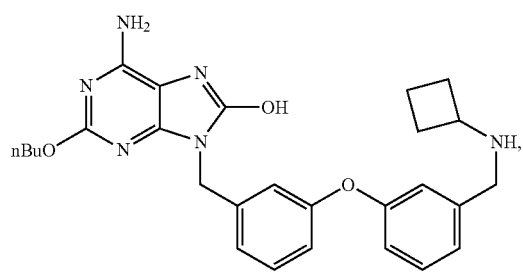
(IIa-02)
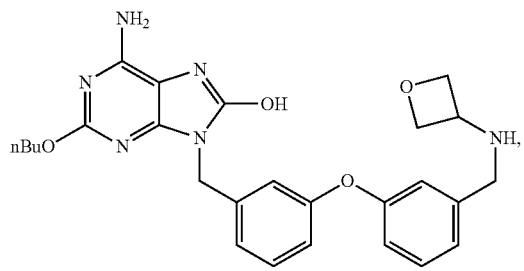
(IIa-03)
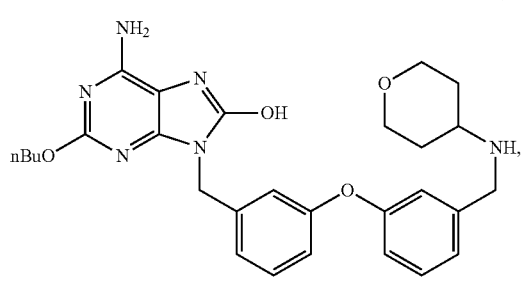
(IIa-04)
(IIa-05)
(IIa-06)
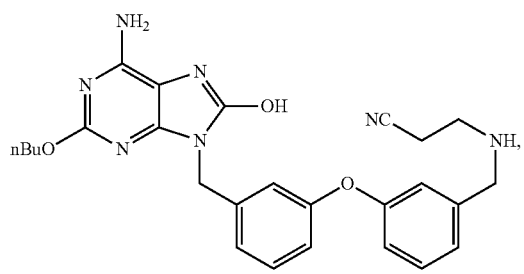
(IIa-07)

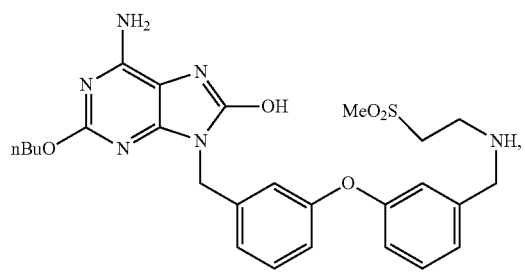

(IIa-08)

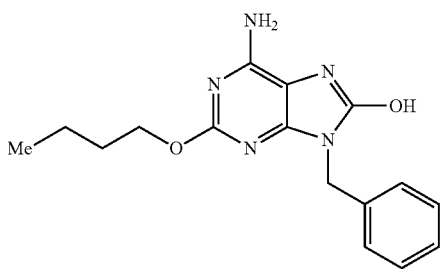

(B)

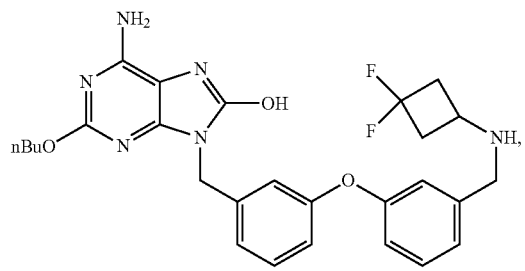

(IIa-09)

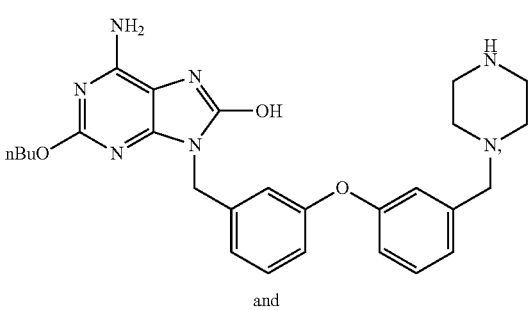

(IIa-10)

and

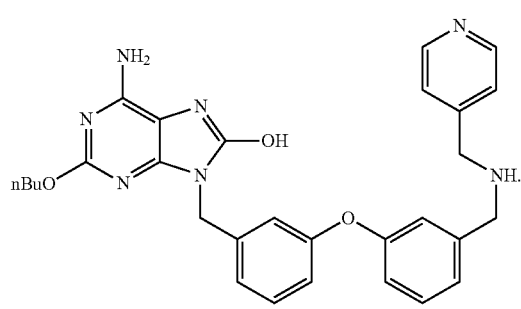

(IIa-11)

Table A presents biological activity data for compounds disclosed herein. One set of data relates TLR7 agonism activity using the HEK-Blue™ TLR7 reporter assay, as described hereinbelow. Another set of data relates to the induction of interleukin 6 (IL-6), a cytokine that plays an important role in the TLR7 pathway. For comparison, activities of resiquimod, vesatolimod, gardiquimod, and Compound B (CAS Reg. No. 226906-84-9) are also presented.

TABLE A

Biological Activity

| Compound | TLR7 Agonism ($EC_{50}$, nM) | IL6 Induction ($EC_{50}$, μM) |
| --- | --- | --- |
| Resiquimod | 420 | — |
| Vesatolimod | 1,200 | — |
| Gardiquimod | 3,340 | — |
| Compound B | 474 | — |
| Ia-01 | 14 | 0.506 |
| Ia-02 | 1.3 | — |
| Ia-03 | 2.1 | 0.0176 |
| Ia-04 | 2.6 | 0.0104 |
| Ia-05 | 1.7 | 0.0310 |
| Ia-06 | 1.4 | 0.0173 |
| Ia-07 | 1.3 | 0.00662 |
| Ia-08 | 13 | 0.0243 |
| Ib-01 | 12 | 0.104 |
| Ib-02 | 1.2 | 0.0296 |
| Ib-03 | 1.1 | 0.00750 |
| Ib-04 | 0.91 | — |
| Ib-05 | 0.70 | 0.00957 |
| Ib-06 | 0.91 | 0.0107 |
| Ib-07 | 0.62 | 0.00581 |
| Ib-08 | 5.3 | — |
| Ib-09 | 1.3 | 0.00591 |
| Ib-10 | 1.3 | 0.0143 |
| Ib-11 | 1.6 | 0.00814 |
| Ib-12 | 0.54 | 0.00377 |
| Ib-13 | 2.9 | 0.0309 |
| Ib-14 | 1.8 | 0.0189 |
| Ib-15 | 1.1 | 0.0647 |
| Ib-16 | 0.35 | 0.0848 |
| Ib-17 | 0.83 | 0.00511 |
| Ic-01 | 2.40 | 0.0101 |
| Ic-02 | 2.51 | 0.0161 |
| Ic-03 | 4.27 | 0.0780 |
| Ic-04 | 1.82 | 0.0207 |
| Ic-05 | 0.871 | 0.0442 |
| Ic-06 | 2.82 | 0.0280 |
| Ic-07 | 3.57 | 0.133 |
| Ic-08 | 8.02 | 0.232 |
| Id-01 | 2.22 | 0.028 |
| Id-02 | 2.07 | 0.025 |
| Id-03 | 1.12 | 0.014 |
| Id-04 | 0.96 | 0.013 |
| Id-05 | 1.6 | 0.012 |
| Id-06 | 1.8 | 0.10 |
| Id-07 | 0.89 | 0.015 |
| Id-08 | 1.77 | 0.021 |
| Ie-01 | 0.45 | 0.026 |
| Ie-02 | 1.38 | 0.019 |
| Ie-03 | 1.12 | 0.019 |
| Ie-04 | 1.8 | 0.46 |
| Ie-05 | 1.14 | 0.024 |
| Ie-06 | 0.46 | 0.029 |
| Ie-07 | 1.71 | 0.13 |
| Ie-08 | 1.2 | 0.0076 |
| Ie-09 | 3.9 | 0.25 |
| Ie-10 | 2.9 | 0.075 |
| If-01 | 7.5 | 0.024 |

TABLE A-continued

Biological Activity

| Compound | TLR7 Agonism (EC$_{50}$, nM) | IL6 Induction (EC$_{50}$, μM) |
|---|---|---|
| If-02 | 5.8 | 0.072 |
| If-03 | 4.3 | 0.014 |
| If-04 | 1.23 | 0.0025 |
| If-05 | 7.46 | 0.017 |
| If-06 | 1.56 | 0.0038 |
| If-07 | 3.20 | 0.0078 |
| If-08 | 1.19 | — |
| If-09 | 0.374 | 0.068 |
| If-10 | 4.20 | — |
| Ig-01 | 72 | 0.31 |
| IIa-01 | 455.4 | — |
| IIa-02 | 435 | — |
| IIa-03 | 403 | — |
| IIa-04 | 113 | — |
| IIa-05 | 375 | — |
| IIa-06 | 121 | — |
| IIa-07 | 279 | — |
| IIa-08 | 154 | — |
| IIa-09 | 525 | — |
| IIa-10 | 942 | — |
| IIa-11 | 431 | — |

Conjugates
General

TLR7 agonists disclosed herein can be delivered to the site of intended action by localized administration or by targeted delivery in a conjugate with a targeting moiety. Preferably, the targeting moiety is an antibody or antigen binding portion thereof and its antigen is found at the locality of intended action, for example a tumor associated antigen if the intended site of action is at a tumor (cancer). Preferably, the tumor associated antigen is uniquely expressed or overexpressed by the cancer cell, compared to a normal cell. The tumor associated antigen can be located on the surface of the cancer cell or secreted by the cancer cell into its environs.

In one aspect, there is provided a conjugate comprising compound of this invention and a ligand, represented by formula (IV)

$$[D(X^D)_a(C)_c(X^Z)_b]_m Z \qquad (IV)$$

where Z is a targeting moiety, D is an agonist of this invention, and —(X$^D$)$_a$C(X$^Z$)$_b$— are collectively referred to as a "linker moiety" or "linker" because they link Z and D. Within the linker, C is a cleavable group designed to be cleaved at or near the site of intended biological action of D; X$^D$ and X$^Z$ are spacer moieties (or "spacers") that space apart D and C and C and Z, respectively; subscripts a, b, and c are independently 0 or 1 (that is, the presence of X$^D$, X$^Z$ and C are optional). Subscript m is 1, 2, 3, 4, 5, 6, 7, 8, 9, or 10 (preferably 1, 2, 3, or 4). D, X$^D$, C, X$^Z$ and Z are more fully described hereinbelow.

By binding to a target tissue or cell where its antigen or receptor is located, Z directs the conjugate there. Cleavage of group C at the target tissue or cell releases D to exert its effect locally. In this manner, precise delivery of D is achieved at the site of intended action, reducing the dosage needed. Also, D is normally biologically inactive (or significantly less active) in its conjugated state, thereby reducing off-target effects.

As reflected by the subscript m, each Z can conjugate with more than one D, depending on the number of sites Z has available for conjugation and the experimental conditions employed. Those skilled in the art will appreciate that, while each individual Z is conjugated to an integer number of Ds, a preparation of the conjugate may analyze for a non-integer ratio of D to Z, reflecting a statistical average. This ratio is referred to as the substitution ratio ("SR") or the drug-antibody ratio ("DAR").

Targeting Moiety Z

Preferably, targeting moiety Z is an antibody. For convenience and brevity and not by way of limitation, the detailed discussion in this specification about Z and its conjugates is written in the context of its being an antibody, but those skilled in the art will understand that other types of Z can be conjugated, mutatis mutandis. For example, conjugates with folic acid as the targeting moiety can target cells having the folate receptor on their surfaces (Leamon et al., Cancer Res. 2008, 68 (23), 9839). For the same reasons, the detailed discussion in this specification is primarily written in terms of a 1:1 ratio of Z to D (m=1).

Antibodies that can be used in conjugates of this invention include those recognizing the following antigens: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. Nos. 8,609,816 B2 (2013; B7H4, also known as O8E; in particular antibodies 2A7, 1G11, and 2F9); Rao-Naik et al., 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Harkins et al., U.S. Pat. No. 7,335,748 B2(2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference. Preferably, the antibody is an anti-mesothelin antibody.

In addition to being an antibody, Z can also be an antibody fragment (such as Fab, Fab', F(ab')$_2$, Fd, or F$_v$) or antibody mimetic, such as an affibody, a domain antibody (dAb), a nanobody, a unibody, a DARPin, an anticalin, a versabody, a duocalin, a lipocalin, or an avimer.

Any one of several different reactive groups on Z can be a conjugation site, including ε-amino groups in lysine residues, pendant carbohydrate moieties, carboxylic acid groups on aspartic or glutamic acid side chains, cysteine-cysteine disulfide groups, and cysteine thiol groups. For reviews on antibody reactive groups suitable for conjugation, see, e.g., Garnett, Adv. Drug Delivery Rev. 2001, 53, 171-216 and Dubowchik and Walker, Pharmacology & Therapeutics 1999, 83, 67-123, the disclosures of which are incorporated herein by reference.

Most antibodies have multiple lysine residues, which can be conjugated via their E-amino groups via amide, urea, thiourea, or carbamate bonds.

A thiol (—SH) group in the side chain of a cysteine can be used to form a conjugate by several methods. It can be used to form a disulfide bond between it and a thiol group on the linker. Another method is via its Michael addition to a maleimide group on the linker.

Typically, although antibodies have cysteine residues, they lack free thiol groups because all their cysteines are engaged in intra- or inter-chain disulfide bonds. To generate a free thiol group, a native disulfide group can be reduced. See, e.g., Packard et al., Biochemistry 1986, 25, 3548; King et al., Cancer Res. 1994, 54, 6176; and Doronina et al., Nature Biotechnol. 2003, 21, 778. Alternatively, a cysteine having a free —SH group can be introduced by mutating the antibody, substituting a cysteine for another amino acid or inserting one into the polypeptide chain. See, for example, Eigenbrot et al., U.S. Pat. No. 7,521,541 B2 (2009); Chilkoti et al., Bioconjugate Chem. 1994, 5, 504; Urnovitz et al., U.S. Pat. No. 4,698,420 (1987); Stimmel et al., J. Biol. Chem. 2000, 275, 30445; Bam et al., U.S. Pat. No. 7,311,902 B2 (2007); Kuan et al., J. Biol. Chem. 1994, 269, 7610; Poon et al., J. Biol. Chem. 1995, 270, 8571; Junutula et al., Nature Biotechnology 2008, 26, 925 and Rajpal et al., U.S. Provisional Application No. 62/270,245, filed Dec. 21, 2015. In yet another approach, a cysteine is added to the C-terminus of the heavy of light chain. See, e.g., Liu et al., U.S. Pat. No. 8,865,875 B2 (2014); Cumber et al., J. Immunol. 1992, 149, 120; King et al, Cancer Res. 1994, 54, 6176; Li et al., Bioconjugate Chem. 2002, 13, 985; Yang et al., Protein Engineering 2003, 16, 761; and Olafson et al., Protein Engineering Design & Selection 2004, 17, 21. The disclosures of the documents cited in this paragraph are incorporated herein by reference.

Linkers and their Components

As noted above, the linker comprises up to three elements: a cleavable group C and optional spacers $X^Z$ and $X^D$.

Group C is cleavable under physiological conditions. Preferably it is relatively stable while the conjugate is in circulation in the blood, but is readily cleaved once the conjugate reaches its site of intended action.

A preferred group C is a peptide that is cleaved selectively by a protease inside the target cell, as opposed to by a protease in the serum. Typically, the peptide comprises from 1 to 20 amino acids, preferably from 1 to 6 amino acids, more preferably from 2 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this specification, the term "amino acid" also includes amino acid analogs and mimetics. Analogs are compounds having the same general H2N(R)CHCO2H structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, C contains an amino acid sequence that is a cleavage recognition sequence for a protease. Many cleavage recognition sequences are known in the art. See, e.g., Matayoshi et al. Science 247: 954 (1990); Dunn et al. Meth. Enzymol. 241: 254 (1994); Seidah et al. Meth. Enzymol. 244: 175 (1994); Thornberry, Meth. Enzymol. 244: 615 (1994); Weber et al. Meth. Enzymol. 244: 595 (1994); Smith et al. Meth. Enzymol. 244: 412 (1994); and Bouvier et al. Meth. Enzymol. 248: 614 (1995); the disclosures of which are incorporated herein by reference.

A group C can be chosen such that it is cleaved by a protease present in the extracellular matrix in the vicinity of a cancer, e.g., a protease released by nearby dying cancer cells or a tumor-associated protease secreted by cancer cells. Exemplary extracellular tumor-associated proteases are plasmin, matrix metalloproteases (MMP), thimet oligopeptidase (TOP) and CD10. See, e.g., Trouet et al., U.S. Pat. No. 7,402,556 B2 (2008); Dubois et al., U.S. Pat. No. 7,425,541 B2 (2008); and Bebbington et al., U.S. Pat. No. 6,897,034 B2 (2005). Cathepsin D, normally lysosomal enzyme found inside cells, is sometimes found in the environs of a tumor, possibly released by dying cancer cells.

For conjugates designed to be by an enzyme, C preferably comprises an amino acid sequence selected for cleavage by proteases such cathepsins B, C, D, H, L and S, especially cathepsin B. Exemplary cathepsin B cleavable peptides include Val-Ala, Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit. (Herein, amino acid sequences are written in the N-to-C direction, as in $H_2N$-$AA^2$-$AA^1$-$CO_2H$, unless the context clearly indicates otherwise.) See Dubowchik et al., Biorg. Med. Chem. Lett. 1998, 8, 3341; Dubowchik et al., Bioorg. Med. Chem. Lett. 1998, 8, 3347; and Dubowchik et al., Bioconjugate Chem. 2002, 13, 855; the disclosures of which are incorporated by reference.

Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu. More preferably, it is a two to three amino acid peptide from the foregoing group.

The preparation and design of cleavable groups C consisting of a single amino acid is disclosed in Chen et al., U.S. Pat. No. 8,664,407 B2 (2014), the disclosure of which is incorporated herein by reference.

Group C can be bonded directly to Z or D; i.e. spacers $X^Z$ or $X^D$, as the case may be, can be absent.

When present, spacer $X^Z$ provides spatial separation between C and Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

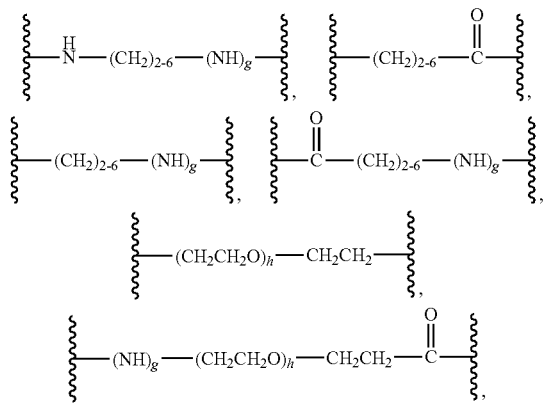

and combinations thereof,
where the subscript g is 0 or 1 and the subscript h is 1 to 24, preferably 2 to 4. These segments can be combined, such as illustrated below:

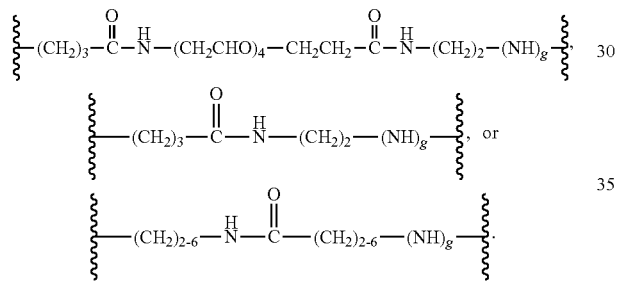

Spacer $X^D$, if present, provides spatial separation between C and D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, analogously to the description above for spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain a poly(ethylene glycol) ("PEG") group. Since the conjugation step typically involves coupling a drug-linker to an antibody in an aqueous medium, a PEG group many enhance the aqueous solubility of the drug-linker. Also, a PEG group may enhance the solubility or reduce aggregation in the resulting ADC. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to C and either Z or D and (2) has a structure such that cleavage from group C initiates a reaction sequence resulting in the self-immolating moiety disbonding itself from Z or D, as the case may be. In other words, reaction at a site distal from Z or D (cleavage from group C) causes the $X^Z$-Z or the $X^D$-D bond to rupture as well. The presence of a self-immolating moiety is desirable in the case of spacer $X^D$ because, if, after cleavage of the conjugate, spacer $X^D$ or a portion thereof were to remain attached to D, the biological activity of D may be impaired. The use of a self-immolating moiety is especially desirable where cleavable group C is a polypeptide, in which instance the self-immolating moiety typically is located adjacent thereto, in order to prevent D from sterically or electronically interfering with peptide cleavage.

Exemplary self-immolating moieties (i)-(v) bonded to a hydroxyl or amino group of D are shown below:

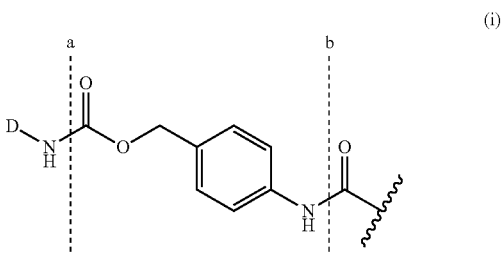

(i)

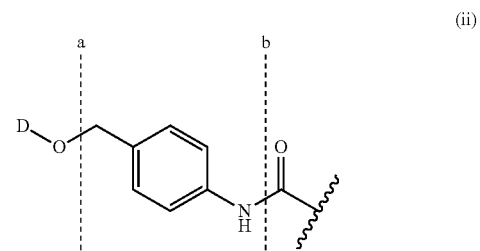

(ii)

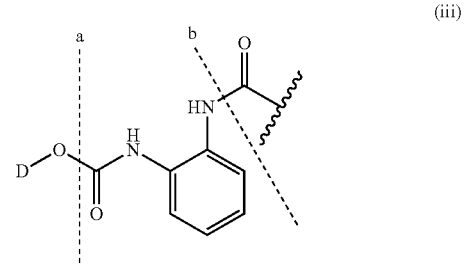

(iii)

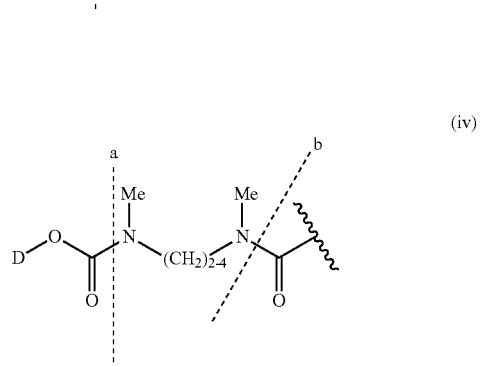

(iv)

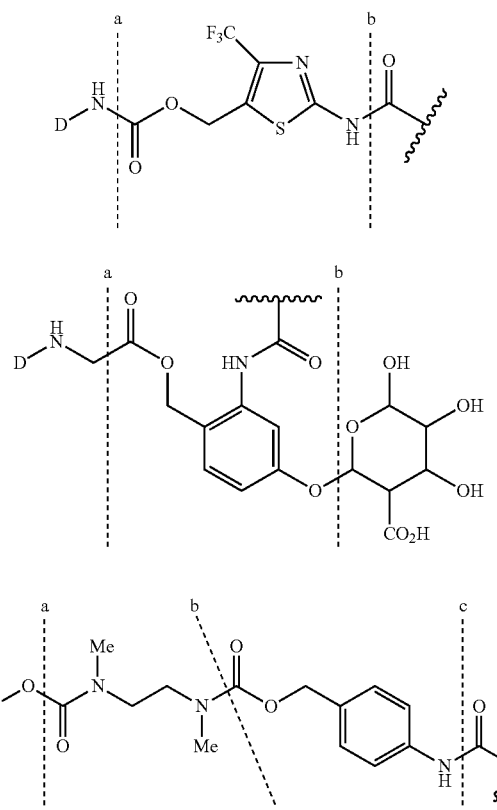

The self-immolating moiety is the structure between dotted lines a and b (or dotted lines b and c), with adjacent structural features shown to provide context. Self-immolating moieties (i) and (v) are bonded to a D-NH$_2$ (i.e., conjugation is via an amino group), while self-immolating moieties (ii), (iii), and (iv) are bonded to a D-OH (i.e., conjugation is via a hydroxyl or carboxyl group). Cleavage of the bond at dotted line b by an enzyme—a peptidase in the instance of structures (i)-(v) and a β-glucuronidase in the instance of structure (vi)—initiates a self-immolating reaction sequence that results in the cleavage of the bond at dotted line a and the consequent release of D-OH or D-NH$_2$, as the case may be. By way of illustration, self-immolating mechanisms for structures (i) and (iv) are shown below:

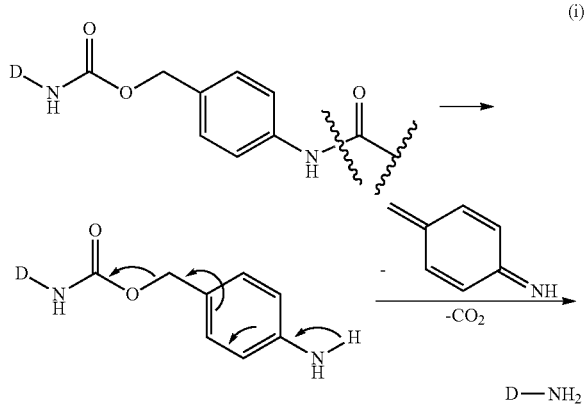

In other words, cleavage of a first chemical bond at one part of a self-immolating group initiates a sequence of steps that results in the cleavage of a second chemical bond—the one connecting the self-immolating group to the drug—at a different part of the self-immolating group, thereby releasing the drug.

In some instances, self-immolating groups can be used in tandem, as shown by structure (vii). In such case, cleavage at dotted line c triggers self-immolation of the moiety between dotted lines b and c by a 1,6-elimination reaction, followed by self-immolation of the moiety between dotted lines a and b by a cyclization-elimination reaction. For additional disclosures regarding self-immolating moieties, see Carl et al., *J. Med. Chem.* 1981, 24, 479; Carl et al., WO 81/01145 (1981); Dubowchik et al., *Pharmacology & Therapeutics* 1999, 83, 67; Firestone et al., U.S. Pat. No. 6,214,345 B1 (2001); Toki et al., *J. Org. Chem.* 2002, 67, 1866; Doronina et al., *Nature Biotechnology* 2003, 21, 778 (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference.

In another embodiment, Z and D are linked by a non-cleavable linker, i.e., C is absent. Metabolism of D eventually reduces the linker to a small appended moiety that does not interfere with the biological activity of D.

Conjugation Techniques

Conjugates of TLR7 agonists disclosed herein preferably are made by first preparing a compound comprising D and linker $(X^D)_a(C)_c(X^Z)_b$ (where $X^D$, C, $X^Z$, a, b, and c are as defined for formula (II)) to form drug-linker compound represented by formula (V):

where $R^{31}$ is a functional group suitable for reacting with a complementary functional group on Z to form the conjugate. Examples of suitable groups $R^{31}$ include amino, azide, thiol, cyclooctyne,

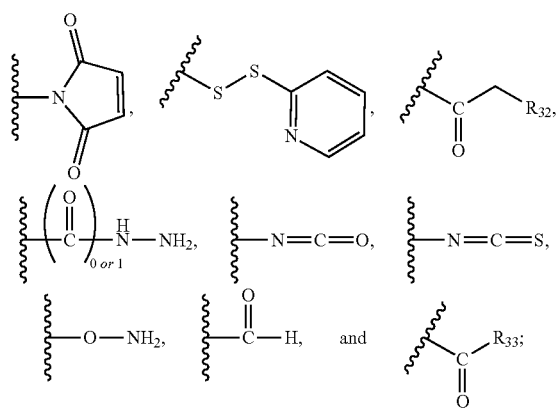

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties D-$(X^D)$aC$(X^Z)$b-$R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., U.S. Pat. No. 8,461,117 B2 (2013); and Chen et al., U.S. Pat. No. 8,664,407 B2 (2014); the disclosures of which are incorporated herein by reference.

Preferably reactive functional group —$R^{31}$ is —NH$_2$, —OH, —CO$_2$H, —SH, maleimido, cyclooctyne, azido (—N$_3$), hydroxylamino (—ONH$_2$) or N-hydroxysuccinimido. Especially preferred functional groups —$R^{31}$ are:

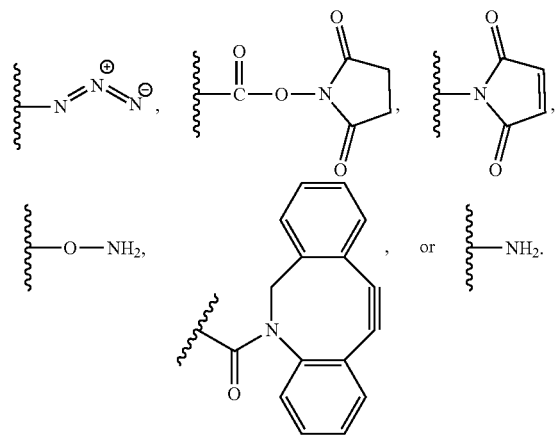

An —OH group can be esterified with a carboxy group on the antibody, for example, on an aspartic or glutamic acid side chain.

A —CO$_2$H group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Where an antibody does not have a cysteine —SH available for conjugation, an ε-amino group in the side chain of a lysine residue can be reacted with 2-iminothiolane or N-succinimidyl-3-(2-pyridyldithio)propionate ("SPDP") to introduce a free thiol (—SH) group—creating a cysteine surrogate, as it were. The thiol group can react with a maleimide or other nucleophile acceptor group to effect conjugation. The mechanism if illustrated below with 2-iminothiolane.

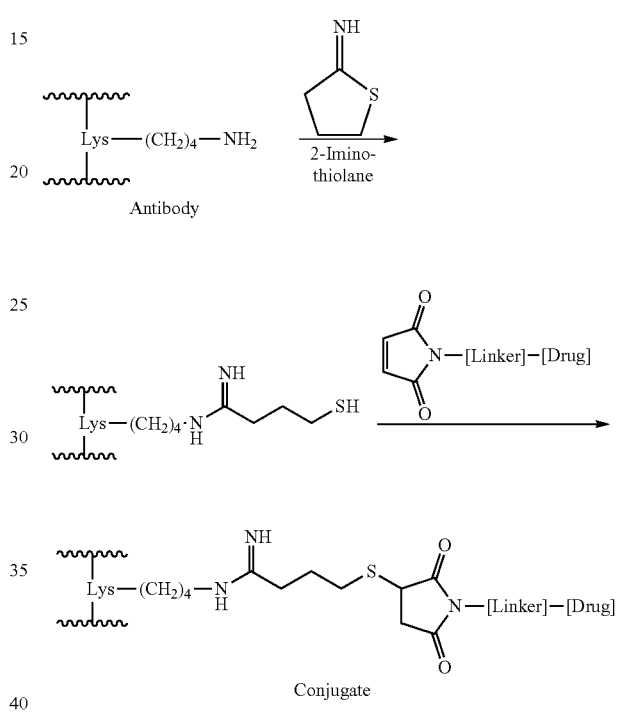

Typically, a thiolation level of two to three thiols per antibody is achieved. For a representative procedure, see Cong et al., U.S. Pat. No. 8,980,824 B2 (2015), the disclosure of which is incorporated herein by reference.

In a reversed arrangement, an antibody Z can be modified with N-succinimidyl 4-(maleimidomethyl)-cyclohexanecarboxylate ("SMCC") or its sulfonated variant sulfo-SMCC, both of which are available from Sigma-Aldrich, to introduce a maleimide group thereto. Then, conjugation can be effected with a drug-linker compound having an —SH group on the linker.

An alternative conjugation method employs copper-free "click chemistry," in which an azide group adds across a strained cyclooctyne to form an 1,2,3-triazole ring. See, e.g., Agard et al., J. Amer. Chem. Soc. 2004, 126, 15046; Best, Biochemistry 2009, 48, 6571, the disclosures of which are incorporated herein by reference. The azide can be located on the antibody and the cyclooctyne on the drug-linker moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

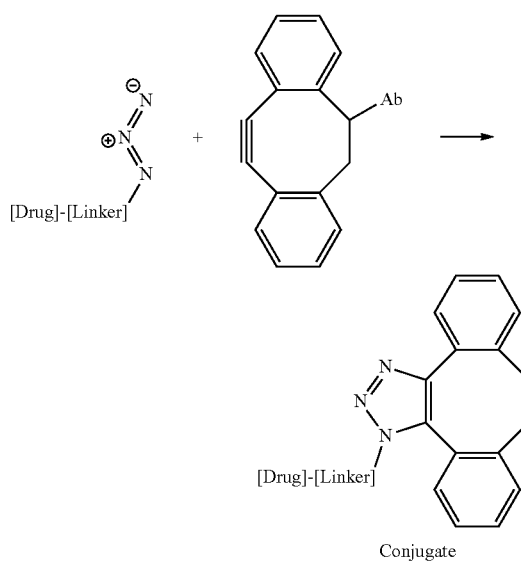

Conjugate

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., Biotechnol. Bioeng. 2009, 102 (2), 400-416. The foregoing disclosures are incorporated herein by reference. Thus, in one embodiment, an antibody that is used for making a conjugate has one or more amino acids replaced by a non-natural amino acid, which preferably is p-acetylphenylalanine orp-azidophenylalanine, more preferably p-acetylphenylalanine.

Still another conjugation technique uses the enzyme transglutaminase (preferably bacterial transglutaminase from *Streptomyces mobaraensis* or BTG), per Jeger et al., *Angew. Chem. Int. Ed.* 2010, 49, 9995. BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

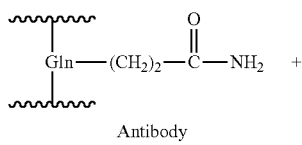

Antibody

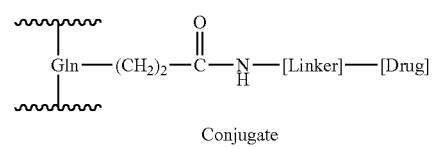

Conjugate

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297; numbering per EU index as set forth in Kabat et al., "Sequences of proteins of immunological interest," 5th ed., Pub. No. 91-3242, U.S. Dept. Health & Human Services, NIH, Bethesda, Md., 1991; hereinafter "Kabat") of the heavy chain—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution not only eliminates glycosylation, but also introduces a second glutamine residue (at position 297) that too is an amine acceptor. Thus, in one embodiment, the antibody is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

An antibody can also be rendered susceptible to BTG-mediated conjugation by introducing into it a glutamine containing peptide, or "tag," as taught, for example, in Pons et al., US 2013/0230543 A1 (2013) and Rao-Naik et al., WO 2016/144608 A1.

In a complementary approach, the substrate specificity of BTG can be altered by varying its amino acid sequence, such that it becomes capable of reacting with glutamine 295 in an umodified antibody, as taught in Rao-Naik et al., WO 2017/059158 A1 (2017).

While the most commonly available bacterial transglutaminase is that from *S. mobaraensis*, transglutaminase from other bacteria, having somewhat different substrate specificities, can be considered, such as transglutaminase from *Streptoverticillium ladakanum* (Hu et al., US 2009/0318349 A1 (2009), US 2010/0099610 A1 (2010), and US 2010/0087371 A1 (2010)).

Figure 5:
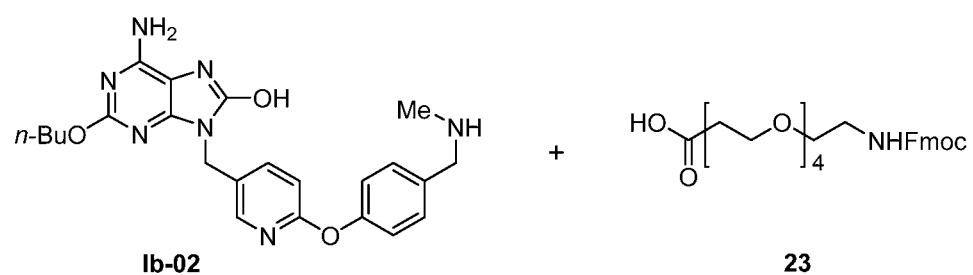
Figure 5:
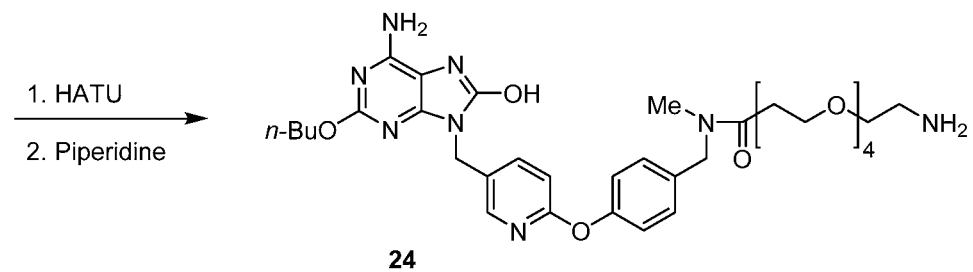

TLR7 agonists of this disclosure having a primary or secondary alkyl amine are particularly suitable for use in conjugates, as the secondary amine provides a functional group for attachment of the linker. An example of such a TLR7 agonist-linker compound is compound 22, which contains an enzymatically cleavable linker. FIG. 5 shows a scheme according to which compound 22 can be prepared.

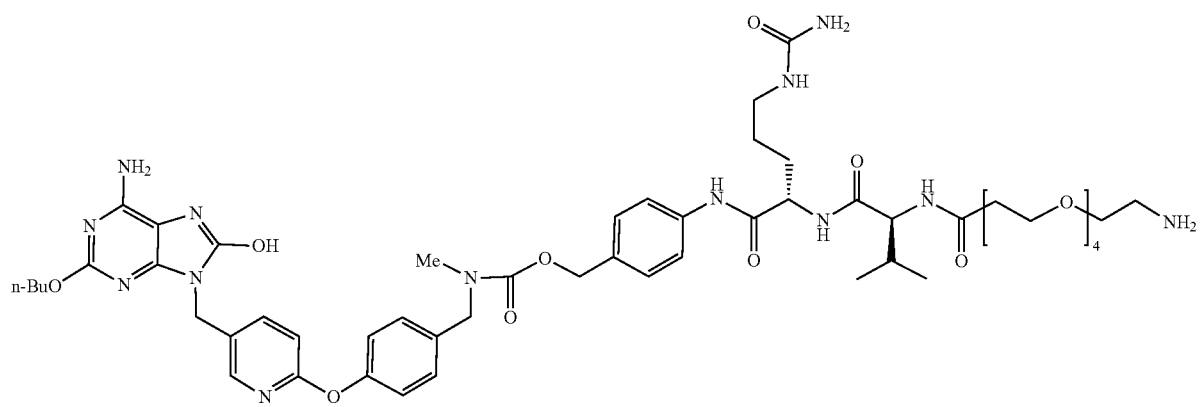

22

Figure 6:
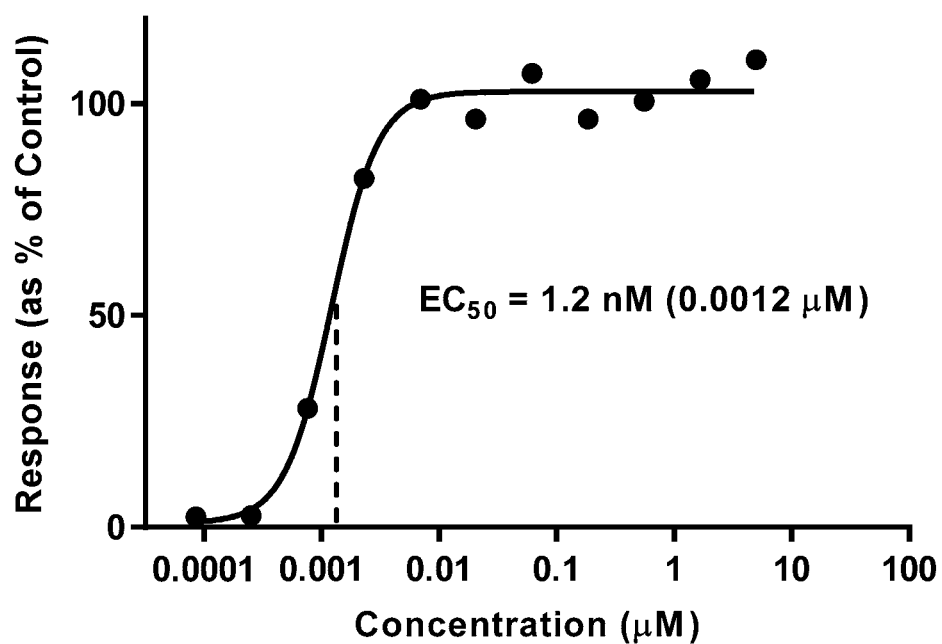
FIG. 6 is a representative graph showing the TLR7 agonism activity of a compound of this invention.

An example of a TLR7 agonist-linker compound that contains a non-enzymatically cleavable linker is compound 24. FIG. 6 shows a scheme for synthesizing compound 24.

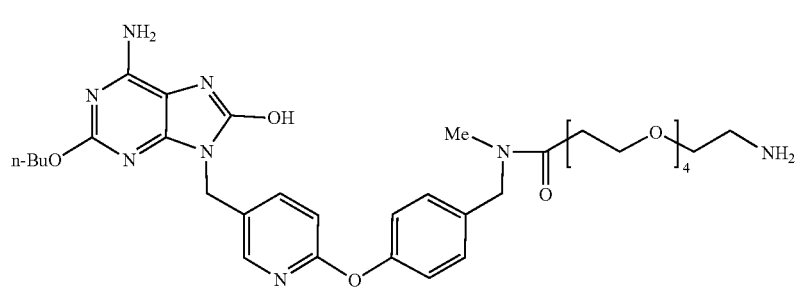

24

Both compounds 22 and 24 contain a primary alkylamino group, rendering them amenable to conjugation with transglutaminase. A suitable conjugation procedure is described in the Examples hereinbelow.

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

TLR7 Agonist Conjugates

Applying the fore-described techniques, TLR7 agonist conjugates such as the ones shown below can be prepared:

Conjugate 1

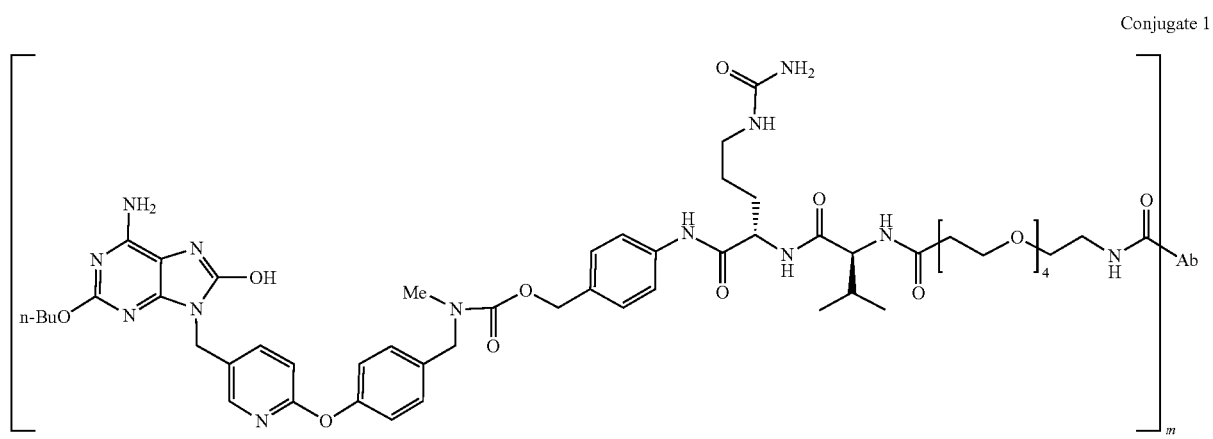

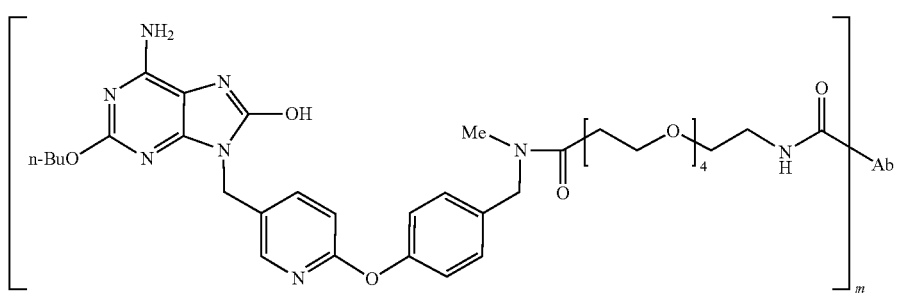

Conjugate 2 where m is 1, 2, 3, or 4 and Ab is an antibody.

Pegylation

Attachment of a poly(ethylene glycol) (PEG) chain to a drug ("PEGylation") can improve the latter's pharmacokinetic properties. The circulation half-life of the drug is increased, sometimes by over an order of magnitude, concomitantly reducing the dosage needed to achieve a desired therapeutic effect. PEGylation can also decrease metabolic degradation of a drug and reduce its immunogenicity. For a review, see Kolate et al., *J. Controlled Release* 2014, 192, 167.

Initially, PEGylation was applied to biologic drugs. As of 2016, over ten PEGylated biologics had been approved. Turecek et al., *J. Pharmaceutical Sci.* 2016, 105, 460. More recently, stimulated by the successful application of the concept to biologics, attention has turned towards its application to small molecule drugs. In addition to the aforementioned benefits, PEGylated small molecule drugs may have increased solubility and cause fewer toxic effects. Li et al. *Prog. Polymer Sci.* 2013, 38, 421.

The compounds disclosed herein can be PEGylated. Where a compound has an aliphatic hydroxyl or aliphatic primary or secondary amine, such as the case of compound Ia-01 or Ia-02 (arrows), it can be PEGylated via an ester, amide, carbonate, or carbamate group with a carboxy-containing PEG molecule utilizing conventional techniques such as dicyclohexylcarbodiimide, HATU, N-hydroxysuccinimide esters, and the like. Various other methods for PEGylating pharmaceutical molecules are disclosed in Alconcel et al., *Polymer Chem.* 2011, 2, 1442, the disclosure of which is incorporated herein by reference.

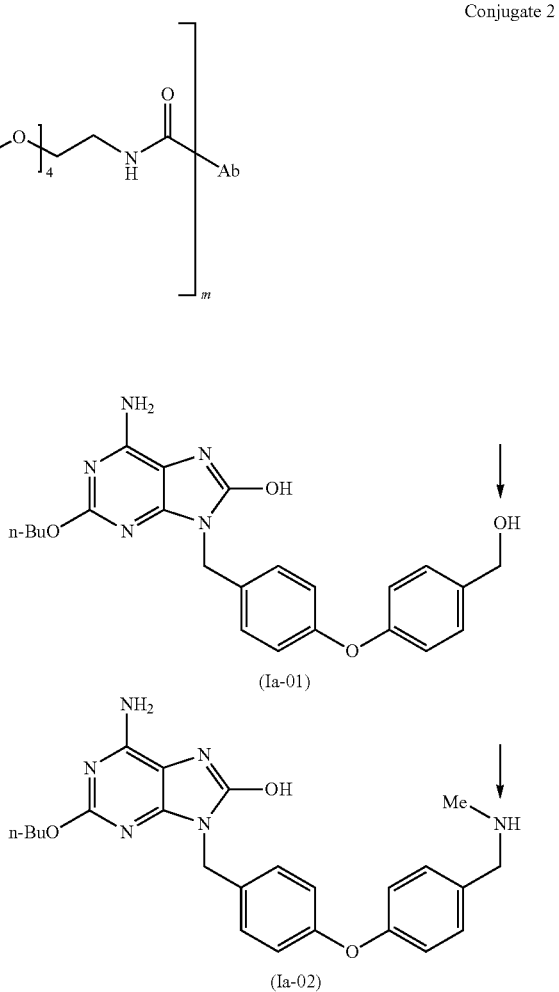

(Ia-01)

(Ia-02)

If desired, a TLR7 agonist disclosed herein can be PEGylated via an enzymatically cleavable linker comprising a self-immolating moiety, to allow release of the un-PEGylated agonist in a designed manner. Further, PEGylation can be combined with conjugation to a protein such as an antibody, if the PEG-containing molecule has a suitable functional group such as an amine for attachment to the protein. The protein can provide an additional therapeutic function or, if an antibody, can provide a targeting function. These concepts are illustrated in the following reaction sequence, where TLR7-NH—R generically represents a TLR7 agonist:

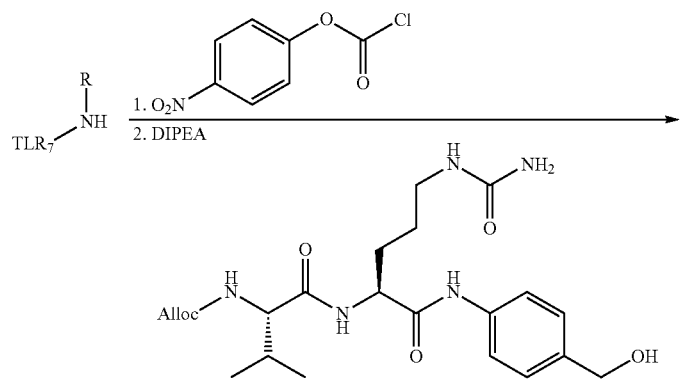

-continued

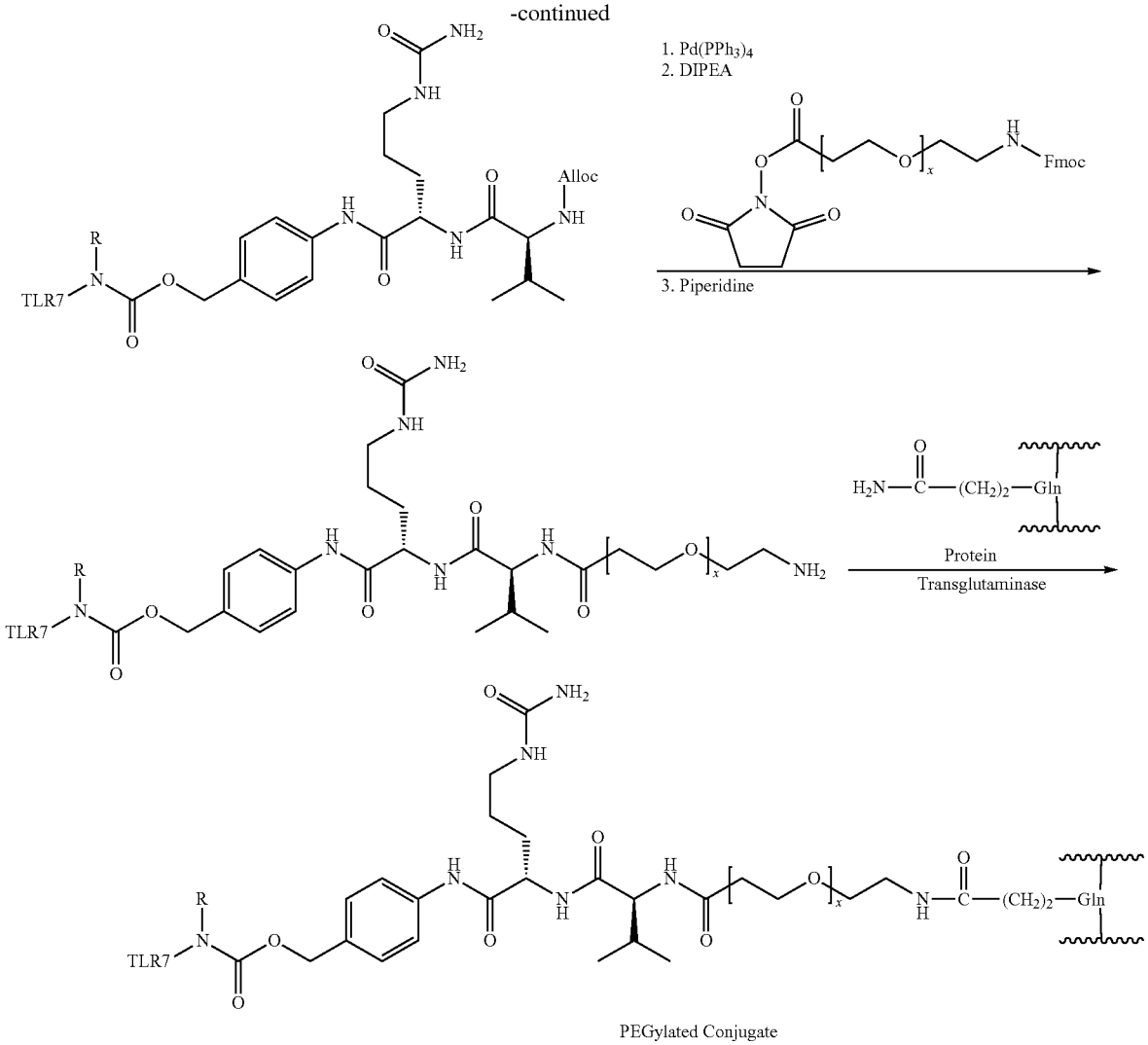

In the above reaction sequence, the valine-citrulline (Val-Cit) dipeptide is cleavable by the enzyme cathepsin B, with a p-aminobenzyl oxycarbonyl (PABC) group serving as a self-immolating spacer. The functional group for conjugation is an amine group, which is temporarily protected by an Fmoc group. Conjugation is effected by the enzyme transglutaminase, with a glutamine (Gln) side chain acting as the acyl acceptor. The subscript x, denoting the number of PEG repeat units, can vary widely, depending on the purpose of the PEGylation, as discussed below. For some purposes, x can be relatively small, such as 2, 4, 8, 12, or 24. For other purposes, x is large, for example between about 45 and about 910.

Those skilled in the art will understand that the sequence is illustrative and that other elements—peptide, self-immolating group, conjugation method, PEG length, etc.—may be employed, as is well known in the art. They will also understand that, while the above sequence combines PEGylation and conjugation, PEGylation does not require conjugation, and vice-versa.

Where the compound lacks aliphatic hydroxyl or aliphatic primary or secondary amine, as in the case of compound 13 (FIG. 2), it still can be PEGylated at the aromatic amine (arrow). A method for PEGylating at this position is disclosed by Zarraga, US 2017/0166384 A1 (2007), the disclosure of which is incorporated by reference.

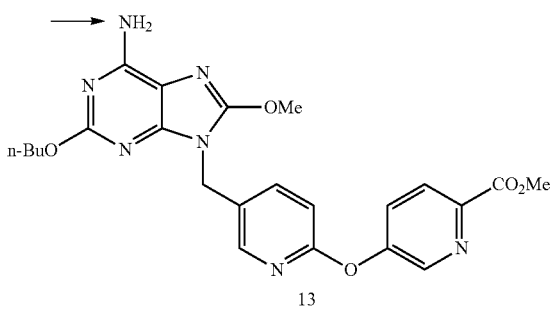

In some embodiments, it may be desirable to have multiple PEGylated agonists linked in a single molecule. For instance, four PEGylated arms can be constructed on pentaerythritol ($C(CH_2OH)_4$) and a TLR7 agonist can be attached to each PEGylated arm. See Gao et al., US 2013/0028857 A1 (2013), the disclosure of which is incorporated by reference.

For modulating pharmacokinetics, it is generally preferred that the PEG moiety have a formula weight of between about 2 kDa (corresponding to about 45 —($CH_2CH_2O$)— repeating units) and between about 40 kDa (corresponding to about 910 —($CH_2CH_2O$)— repeating units), more preferably between about 5 kDa and about 20 kDa. That is, the range of the subscript x in the above formulae is from about 45 to about 910. It is to be understood that PEG compositions are not 100% homogeneous but, rather, exhibit a distribution of molecular weights. Thus, a reference to, for example, "20 kDa PEG" means PEG having an average molecular weight of 20 kDa.

PEGylation can also be used for improving the solubility of an agonist. In such instances a shorter PEG chain can be used, for example comprising 2, 4, 8, 12, or 24 repeating units.

EXAMPLES

The practice of this invention can be further understood by reference to the following examples, which are provided by way of illustration and not of limitation.

Example 1—Series (Ia) and (Ib) Compounds

This example and FIG. 1 relate to the synthesis of series (Ia) and (Ib) compounds, with compound (Ib-02) being used as an exemplar.

COMPOUND 3. A suspension of methyl 4-hydroxybenzoate 2 (2 g, 13.15 mmol), 6-fluoronicotinaldehyde 1 (1.809 g, 14.46 mmol) and $K_2CO_3$ (1.998 g, 14.46 mmol) in DMF (26.3 mL) was stirred at 110° C. for 4 h. LCMS indicated the reaction was complete. Upon cooling, the reaction was quenched with water and the resulting solid was collected by filtration and rinsed with water and dried in vacuo to yield compound 3, (3.30 g, 12.84 mmol, 95.1% yield). LCMS ESI: calculated for $C_{14}H_{11}NO_4$=258.1 (M+H$^+$), found 258.0 (M+H$^+$). $^1$H NMR (400 MHz, CHLOROFORM-d) δ 10.01 (s, 1H), 8.63 (d, J=2.4 Hz, 1H), 8.23 (dd, J=8.6, 2.4 Hz, 1H), 8.17-7.97 (m, 2H), 7.27-7.22 (m, 2H), 7.10 (d, J=8.6 Hz, 1H), 3.93 (s, 3H)

COMPOUND 4. A solution of compound 3 (3.76 g, 14.62 mmol) in MeOH (100 ml) was treated with NaBH$_4$ (0.553 g, 14.62 mmol) in portions at 0° C., then stirred for 10 mins while bath was still in place. LCMS indicated the reaction was complete. The reaction was quenched by slowly adding half-saturated NH$_4$C$_1$. The reaction mixture stirred for 30 mins at RT and extracted with EtOAc. The organic extracts were dried over Na$_2$SO$_4$, filtered, and concentrated. The crude solid was slurried into water and collected by filtration and dried in vacuo to yield compound 4 (3.37 g, 13.00 mmol, 89% yield). LCMS ESI: calculated for $C_{14}H_{13}NO_4$=260.1 (M+H$^+$), found 260.0(M+H$^+$). $^1$H NMR (400 MHz, CHLOROFORM-d) δ 8.21 (d, J=2.2 Hz, 1H), 8.12-8.04 (m, 2H), 7.81 (dd, J=8.4, 2.4 Hz, 1H), 7.21-7.13 (m, 2H), 6.99 (d, J=8.4 Hz, 1H), 4.71 (s, 2H), 3.91 (s, 3H)

COMPOUND 5. A suspension of compound 4 (0.2 g, 0.771 mmol) in THF (3.86 ml) was treated with triphenylphosphine (0.223 g, 0.849 mmol), followed by N-bromosuccinimide (NBS, 0.165 g, 0.926 mmol). After stirred at RT for 60 min, the reaction was complete. The reaction was quenched with water and the reaction mixture was extracted with EtOAc. The organic extracts were dried over Na$_2$SO$_4$, filtered, and concentrated The crude product was purified on a 12 g silica column, eluted with 0-80% EtOAc/hexane to yield compound 5 (0.15 g, 0.466 mmol, 60.4% yield). LCMS ESI: calculated for $C_{14}H_{12}BrNO_3$=322.0 (M+H$^+$), found 321.9 (M+H$^+$). $^1$H NMR (400 MHz, CHLOROFORM-d) δ 8.21 (d, J=2.4 Hz, 1H), 8.15-8.01 (m, 2H), 7.80 (dd, J=8.5, 2.5 Hz, 1H), 7.23-7.13 (m, 2H), 6.97 (d, J=8.6 Hz, 1H), 4.47 (s, 2H), 3.92 (s, 3H).

COMPOUND 7. A suspension of 2-butoxy-8-methoxy-9H-purin-6-amine 6 (CAS Reg. No. 866268-31-7, in TFA, 562 mg, 1.600 mmol) and cesium carbonate (1.67 g, 5.12 mmol) in DMF (20 mL) was treated with compound 5 (567 mg, 1.760 mmol). The reaction mixture was stirred at RT for 3 h. LCMS indicated the reaction was completed. The reaction was quenched with saturated NH$_4$C$_1$ and extracted with EtOAc. The organic extracts were dried over Na$_2$SO$_4$, filtered and concentrated. The crude product was purified on a 40 g silica column, eluting with 20% MeOH in DCM (0-40% gradient). The desired fractions were concentrated to yield compound 7 (478 mg, 0.999 mmol, 62.4% yield). LCMS ESI: calculated for $C_{24}H_{26}N_6O_5$=479.2 (M+H$^+$), found 479.1 (M+H$^+$). $^1$H NMR (400 MHz, CHLOROFORM-d) δ 8.25 (d, J=2.2 Hz, 1H), 8.11-8.01 (m, 2H), 7.78 (dd, J=8.4, 2.4 Hz, 1H), 7.17-7.06 (m, 2H), 6.91 (d, J=8.4 Hz, 1H), 5.06 (s, 2H), 4.32 (t, J=6.6 Hz, 2H), 4.11 (s, 3H), 3.95-3.84 (m, 3H), 3.49 (s, 2H), 1.89-1.70 (m, 2H), 1.63-1.34 (m, 2H), 0.97 (t, J=7.4 Hz, 3H)

COMPOUND 8. A stirred solution of ester 7 (0.46 g, 0.934 mmol) in THF (10 mL) was treated dropwise with LiAlH$_4$ (1.0 M in THF; 1.401 mL, 1.401 mmol) at 0° C. After stirring for 3 h. LCMS indicated the reaction was complete. Na$_2$SO$_4$.10 H$_2$O was added slowly. After stirring for 1 h, the solid was filtered off and rinsed with MeOH. The filtrate was concentrated. The crude product was purified on a 40 g silica column, eluting with 20% MeOH in DCM (0-40% gradient). The desired fractions were concentrated to yield compound 8 (363 mg, 0.806 mmol, 86% yield). LCMS ESI: calculated for $C_{24}H_{26}N_6O_5$=451.2 (M+H$^+$), found 451.1 (M+H$^+$). $^1$H NMR (400 MHz, CHLOROFORM-d) δ 8.22 (d, J=2.2 Hz, 1H), 7.73 (dd, J=8.5, 2.5 Hz, 1H), 7.40 (d, J=8.4 Hz, 2H), 7.10 (d, J=8.4 Hz, 2H), 6.86 (d, J=8.4 Hz, 1H), 5.82-5.39 (m, 1H), 5.04 (s, 2H), 4.70 (s, 2H), 4.33 (t, J=6.7 Hz, 2H), 4.10 (s, 3H), 1.86-1.73 (m, 2H), 1.50 (dq, J=15.0, 7.5 Hz, 2H), 1.01-0.87 (m, 3H)

COMPOUND Ib-01. A suspension of compound 8 (363 mg, 0.806 mmol) in THF (10 mL) was treated with HCl (1.0 M in water, 2 mL, 2.000 mmol). After stirring at 60° C. for 4 h, LCMS indicated the reaction was done. Upon cooling, a white solid was precipitated out. It was collected by filtration, rinsed with water and dried in vacuo to yield compound Ib-01 (263.6 mg, 0.598 mmol, 74.2% yield). LCMS ESI: calculated for $C_{22}H_{24}N_6O_4$=437.2 (M+H$^+$), found 437.1 (M+H$^+$). $^1$H NMR (400 MHz, METHANOL-d$_4$) δ 8.28 (d, J=2.4 Hz, 1H), 7.94 (dd, 2.4 Hz, 1H), 7.42 (d, J=8.6 Hz, 2H), 7.08 (d, J=8.4 Hz, 2H), 6.94 (d, J=8.6 Hz, 1H), 5.06 (s, 2H), 4.63 (s, 2H), 4.54 (t, J=6.5 Hz, 2H), 1.99-1.61 (m, 2H), 1.64-1.34 (m, 2H), 1.01 (t, J=7.4 Hz, 3H).

COMPOUND Ib-02. A solution of compound Ib-01(100 mg, 0.229 mmol) in THF (10 mL) was treated with thionyl chloride (0.334 mL, 4.58 mmol) at RT and stirred for 3 h, after which the reaction was complete by LCMS. The excess thionyl was removed azeotropically with DCM. The resulting chloromethyl compound was directly carried over to next step without purification.

A stirred solution of the chloromethyl compound (15 mg, 0.033 mmol) in DMF (0.5 mL) was treated with methyl amine (2.0 M in THF, 0.165 mL, 0.330 mmol) and stirred at RT overnight, after which the reaction was complete. The reaction mixture was diluted with 50% MeOH in DMF and the precipitated solid was filtered off. The crude filtrate was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 7-47% B over 20 minutes, then a 4-minute hold at 100% B; Flow: 20 mL/min. Fractions containing the desired product were combined and dried via centrifugal evaporation to yield compound Ib-02 (3.7 mg, 7.08 μmol, 21.47% yield). LCMS ESI: calculated for $C_{23}H_{27}N_7O_3$=450.2 (M+H$^+$), found 450.2 (M+H$^+$). $^1$H NMR (500 MHz, DMSO-d$_6$) δ 8.15 (s, 1H), 7.80 (dd, J=8.4, 2.0 Hz, 1H), 7.37 (d, J=8.2 Hz, 2H), 7.07 (d, J=8.3 Hz, 2H), 6.97 (d, J=8.5 Hz, 1H), 6.36 (s, 2H), 4.86 (s, 2H), 4.18 (t, J=6.6 Hz, 2H), 3.77 (s, 2H), 2.37 (s, 3H), 1.71-1.56 (m, 2H), 1.47-1.34 (m, 2H), 0.92 (t, J=7.4 Hz, 3H).

Generally following the preceding procedures, additional compounds in the (Ib) series were prepared, as shown in Table B below, using alternative amines.

TABLE B

Additional Compounds (Ib)

| Compound Number | Amine | Expected Mass (M + H) | Observed Mass (M + H) |
|---|---|---|---|
| Ib-03 | Me₂CHNH₂ (isopropylamine structure) | 478.2 | 478.1 |
| Ib-04 | cyclobutyl-NH₂ | 490.2 | 490.0 |
| Ib-05 | oxetan-3-yl-NH₂ | 492.2 | 492.1 |
| Ib-06 | HO-CH₂CH₂-NH₂ | 480.2 | 480.3 |
| Ib-07 | MeO-CH₂CH₂-NH₂ | 494.2 | 494.1 |
| Ib-08 | C₆H₅-CH₂-NH₂ | 526.2 | 526.1 |
| Ib-09 | bicyclo[1.1.1]pentyl-NH₂ | 502.2 | 502.3 |
| Ib-10 | 3,3-difluorocyclobutyl-NH₂ | 526.2 | 526.3 |
| Ib-11 | cyclopentyl-NH₂ | 504.3 | 504.2 |
| Ib-12 | Me₂CHCH₂-NH₂ (isobutylamine) | 492.3 | 492.3 |
| Ib-13 | F₂HC-CH₂-NH₂ | 500.2 | 500.2 |
| Ib-14 | MeO₂S-CH₂CH₂-NH₂ | 542.2 | 542.0 |
| Ib-15 | cyclopropyl-CH₂-NH₂ | 490.0 | 490.3 |
| Ib-16 | NC-CH₂CH₂-NH₂ | 489.2 | 489.3 |
| Ib-17 | cyclopropyl-NH₂ | 476.2 | 476.1 |

Those skilled in the art will appreciate that further compounds can be made following the above procedures, mutatis mutandis. For example the compound

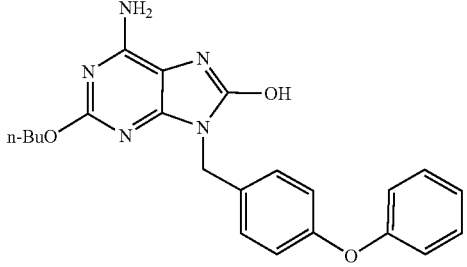

can be made by using as a starting material phenol instead of methyl 4-hydroxybenzoate in the scheme of FIG. 1.

The compound

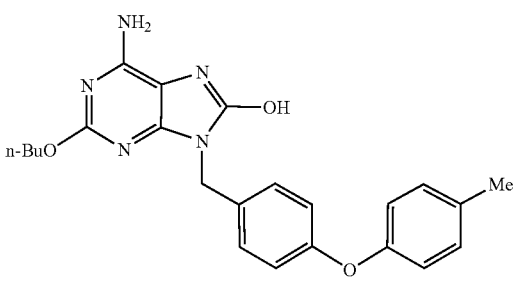

can be made by complete reduction of the methyl ester group in compound 7 of FIG. 1.

Compounds in the Ia series were made using 4-fluorobenzaldehyde instead of 6-fluoronicotinealdehyde in the scheme of FIG. 1 and generally following the procedures described above.

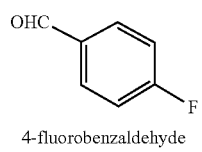

4-fluorobenzaldehyde

Compounds (Ia) so made are listed in Table C.

TABLE C

| | Compounds (Ia) | | |
|---|---|---|---|
| | | Mass Spectrum | |
| Compound Number | Amine | Expected Mass (M + H) | Observed Mass (M + H) |
| Ia-01 | n/a | 434.2 (M-H) | 434.2 (M-H) |
| Ia-02 | MeNH₂ | 449.2 | 449.1 |
| Ia-03 | cyclopropyl-CH₂-NH₂ | 475.2 | 475.3 |
| Ia-04 | cyclobutyl-CH₂-NH₂ | 489.3 | 489.1 |
| Ia-05 | oxetan-3-yl-CH₂-NH₂ | 491.2 | 491.1 |
| Ia-06 | HO-CH₂CH₂-NH₂ | 479.2 | 479.1 |
| Ia-07 | MeO-CH₂CH₂-NH₂ | 493.2 | 493.2 |
| Ia-08 | C₆H₅-CH₂CH₂-NH₂ | 525.3 | 525.1 |

Example 2—Series (Ic), (Id), (Ie), and (IIa) Compounds

Figure 2:
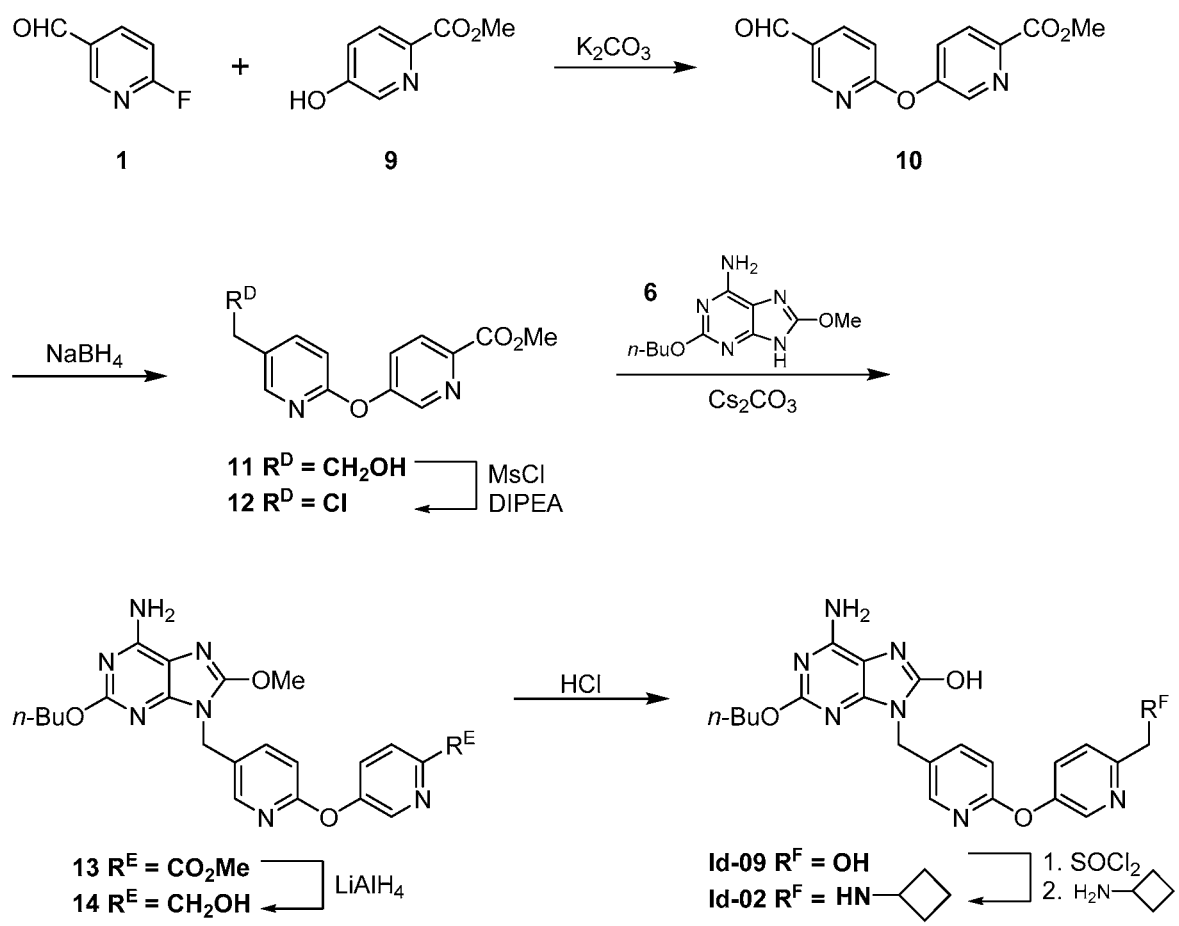

This example and FIG. 2 relate to the synthesis of series (Ic), (Id), (Ie), and (IIa) compounds, with compound (Id-02) being used as an exemplar.

With one exception, the steps in FIG. 2 parallel those in FIG. 1 and the previous example and procedures described above can be applied, mutatis mutandis, in this example. The one exception is that a benzyl chloride compound 12 is prepared in the third step, instead of a benzyl bromide compound 5 (in FIG. 1). The detailed procedure for this step is provided following: To a stirred solution of compound 11 (1.28 g, 4.92 mmol) in DCM (20 mL) was added DIPEA (0.988 mL, 5.66 mmol), followed by Ms-Cl (0.422 mL, 5.41 mmol) at 0° C., followed by stirring at RT for 16 h, after which the reaction was complete. the reaction was quenched with water and extracted with DCM three times. The combined organic extracts were dried over Na₂SO₄, filtered and concentrated to yield compound 12 (1.35 g, 4.84 mmol, 98% yield), which was carried over to next step without purification.

Table D shows the compounds in the (Id) series prepared following the procedure of FIG. 2 and using the indicated amines in the final step.

TABLE D

| | Compounds (Id) | | |
|---|---|---|---|
| | | Mass Spectrum | |
| Compound Number | Amine | Expected Mass (M + H) | Observed Mass (M + H) |
| (Id-01) | isobutylamine (Me₂CH-CH₂-NH₂) | 493.3 | 493.1 |
| (Id-02) | cyclobutyl-CH₂-NH₂ | 491.2 | 490.9 |
| (Id-03) | 4-aminotetrahydropyran | 521.3 | 521.3 |
| (Id-04) | MeO-CH₂CH₂-NH₂ | 495.2 | 495.1 |
| (Id-05) | HO-CH₂CH₂-NH₂ | 481.2 | 481.3 |
| (Id-06) | F₂HC-CH₂-NH₂ | 501.2 | 501.2 |
| (Id-07) | morpholine | 507.2 | 506.9 |
| (Id-08) | N-methylpiperazine | 520.3 | 520.0 |

Compounds in the (Ic) series were prepared generally following the procedures of FIG. 2 for series (Id) compounds, except that 4-hydroxybenzaldehyde and methyl-6-fluoropicolinate were used as starting materials, instead of 6-fluoronicotinaldehyde 1 and methyl 5-hydroxypicolinate 9.

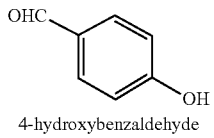
4-hydroxybenzaldehyde

methyl 6-fluoropicolinate

Table E shows the compounds in the (Ic) series prepared in this manner.

TABLE E

Compounds (Ic)

| Compound Number | Amine | Expected Mass (M + H) | Observed Mass (M + H) |
|---|---|---|---|
| (Ic-01) | Me-CH(Me)-CH2-NH2 | 492.2 | 492.3 |
| (Ic-02) | cyclobutyl-NH2 | 490.2 | 490.3 |
| (Ic-03) | oxetan-3-yl-NH2 | 492.2 | 492.3 |
| (Ic-04) | morpholine (HN-O) | 520.3 | 520.1 |
| (Ic-05) | HO-CH2CH2-NH2 | 480.2 | 480.3 |
| (Ic-06) | MeO-CH2CH2-NH2 | 494.2 | 494.3 |
| (Ic-07) | NC-CH2CH2-NH2 | 489.2 | 489.2 |
| (Ic-08) | piperazine (HN-NH) | 505.3 | 505.2 |

Compounds in the (Ie) series were prepared generally following the procedures of FIG. 2 for series (Id) compounds, except that 3,4-difluorobenzaldehyde and methyl 4-hydroxybenzoate were used as starting materials, instead of 6-fluoronicotinaldehyde 1 and methyl 5-hydroxypicolinate 9.

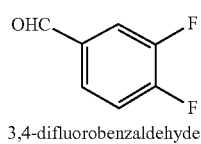
3,4-difluorobenzaldehyde

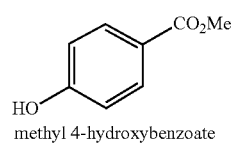
methyl 4-hydroxybenzoate

Table F shows the compounds in the (Ie) series prepared in this manner.

TABLE F

Compounds (Ie)

| Compound Number | Amine | Expected Mass (M + H) | Observed Mass (M + H) |
|---|---|---|---|
| (Ie-01) | Me-CH(Me)-CH2-NH2 | 509.3 | 509.1 |
| (Ie-02) | cyclobutyl-NH2 | 507.2 | 507.1 |
| (Ie-03) | azetidine | 493.2 | 493.1 |
| (Ie-04) | F2HC-CH2-NH2 | 517.2 | 517.3 |
| (Ie-05) | MeO-CH2CH2-NH2 | 511.3 | 511.0 |
| (Ie-06) | HO-CH2CH2-NH2 | 497.2 | 497.3 |
| (Ie-07) | MeO2S-CH2CH2-NH2 | 559.2 | 559.1 |
| (Ie-08) | tetrahydropyran-4-amine | 537.3 | 537.1 |
| (Ie-09) | morpholine (HN-O) | 523.2 | 523.3 |
| (Ie-10) | N-methylpiperazine (HN-N-Me) | 536.3 | 536.0 |

Compounds in the (IIa) series were prepared generally following the procedures of FIG. 2 for series (Id) compounds, except that 3-fluorobenzaldehyde and methyl 3-hydroxybenzoate were used as starting materials, instead of 6-fluoronicotinaldehyde 1 and methyl 5-hydroxypicolinate 9.

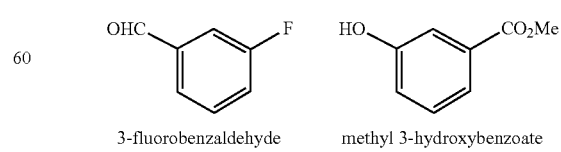
3-fluorobenzaldehyde     methyl 3-hydroxybenzoate

Table G shows the compounds in the (IIa) series prepared in this manner.

TABLE G

Compounds (IIa)

| Compound Number | Amine | Expected Mass (M + H) | Observed Mass (M + H) |
|---|---|---|---|
| (IIa-01) | MeNH$_2$ | 449.2 | 449.3 |
| (IIa-02) | cyclobutyl-NH$_2$ | 489.2 | 489.3 |
| (IIa-03) | 3-aminooxetane | 491.2 | 491.3 |
| (IIa-04) | 4-aminotetrahydropyran | 519.3 | 519.4 |
| (IIa-05) | HO-CH$_2$CH$_2$-NH$_2$ | 479.2 | 479.3 |
| (IIa-06) | MeO-CH$_2$CH$_2$-NH$_2$ | 493.2 | 493.3 |
| (IIa-07) | NC-CH$_2$CH$_2$-NH$_2$ | 488.2 | 488.3 |
| (IIa-08) | MeO$_2$S-CH$_2$CH$_2$-NH$_2$ | 541.2 | 541.4 |
| (IIa-09) | 3-amino-1,1-difluorocyclobutane | 525.2 | 525.3 |
| (IIa-10) | piperazine | 504.3 | 504.3 |
| (IIa-11) | 4-(aminomethyl)pyridine | 526.2 | 526.4 |

Example 3—Series (If) Compounds

Figure 3:
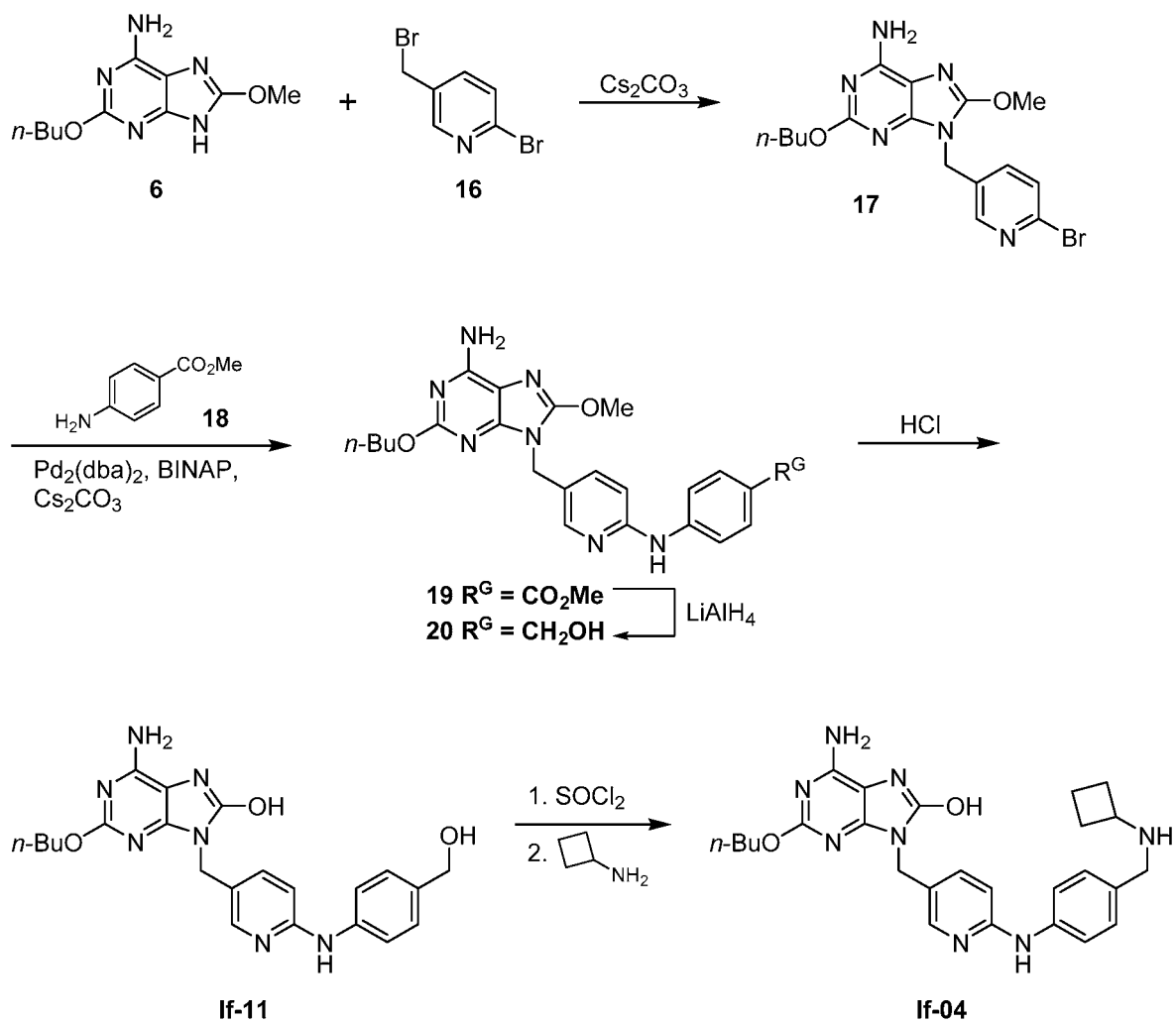
Figure 4:
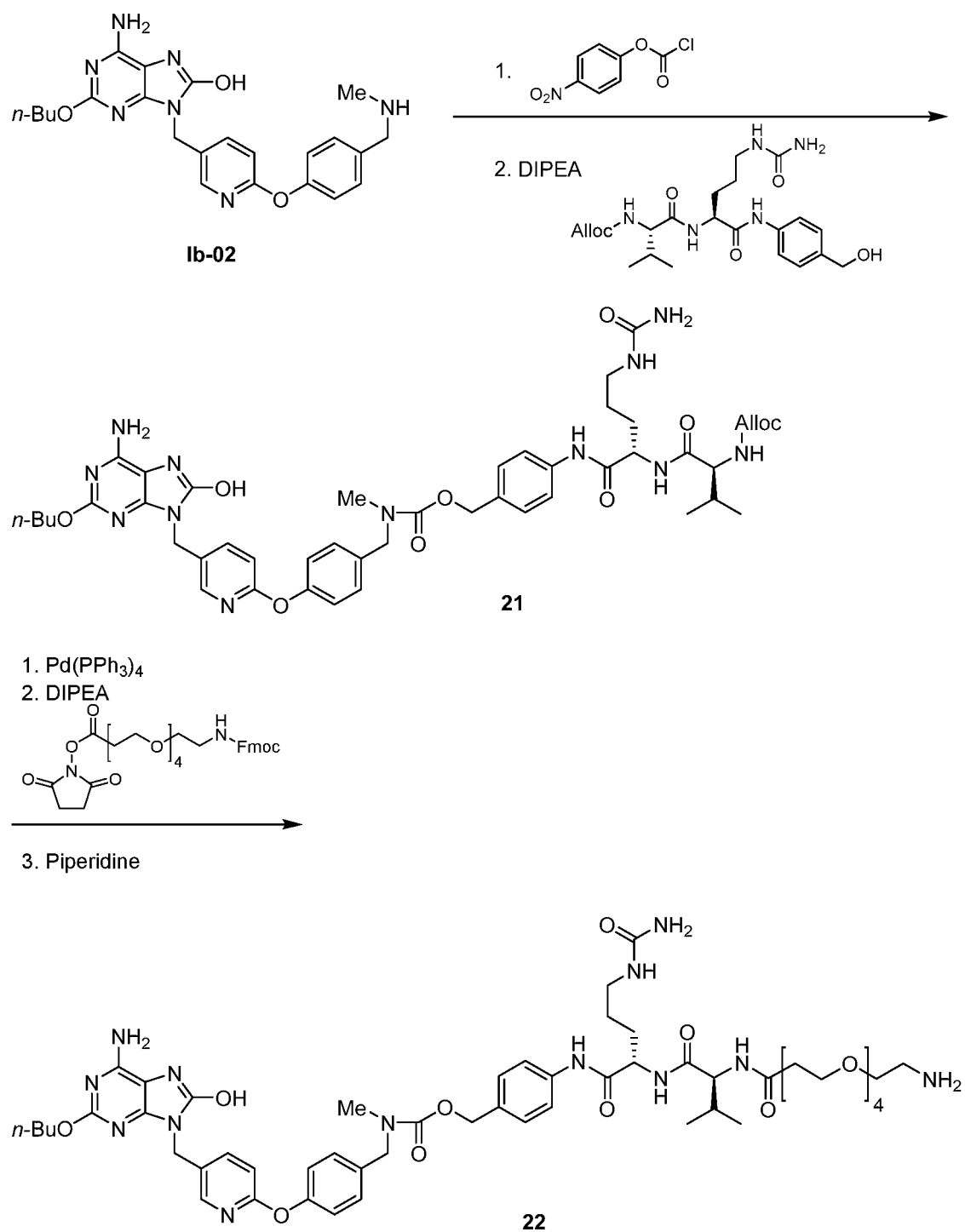
FIG. 4 and FIG. 5 show schemes for the attachment of linkers to compounds of this disclosure, rendering them suitable for conjugation.

This example and FIG. 3 relate to the synthesis of series (If) compounds, with compound (If-04) used as an exemplar.

Compounds 6 and 16 were coupled with Cs$_2$CO$_3$ to afford compound 17.

A mixture of compound 17 (1.05 g, 2.58 mmol), methyl 4-aminobenzoate 18 (0.468 g, 3.09 mmol), Pd$_2$(dba)$_3$ CHCl$_3$ adduct (0.264 g, 0.258 mmol), BINAP (0.321 g, 0.516 mmol) and Cs$_2$CO$_3$ (2.52 g, 7.73 mmol) in dioxane (15 mL) was bubbled with N2 for 5 mins, then sealed, stirred at 100° C. for 5 h, after which the reaction was complete. The reaction mixture was diluted with ethyl acetate and the solid was removed by filtration. The filtrate was concentrated. The crude product was purified on an ISCO silica 12 g column, eluting with 20% MeOH in DCM (DCM gradient 0-20%). The desired fractions were concentrated to yield compound 19 (342.7 mg, 0.718 mmol, 27.8%).

Generally following preceding procedures and the scheme of FIG. 3, compound 19 was used to prepare compounds in the (If) series using the amines shown in Table H.

TABLE H

Compounds (If)

| Compound Number | Amine | Expected Mass (M + H) | Observed Mass (M + H) |
|---|---|---|---|
| (If-01) | isobutylamine (Me$_2$CHCH$_2$NH$_2$) | 491.3 | 491.0 |
| (If-02) | HO-CH$_2$CH$_2$-NH$_2$ | 479.2 | 479.0 |
| (If-03) | 4-aminotetrahydropyran | 519.3 | 519.0 |
| (If-04) | cyclobutyl-NH$_2$ | 489.3 | 489.4 |
| (If-05) | F$_2$HC-CH$_2$-NH$_2$ | 499.2 | 499.1 |
| (If-06) | pyrrolidine | 489.3 | 489.1 |
| (If-07) | 2-amino-2-methyl-1-propanol (Me$_2$C(OH)CH$_2$NH$_2$) | 507.3 | 507.2 |
| (If-08) | MeO-CH$_2$CH$_2$-NH$_2$ | 493.3 | 493.5 |
| (If-09) | MeO$_2$S-CH$_2$CH$_2$-NH$_2$ | 541.2 | 541.1 |
| (If-10) | 1-methylpiperazine | 518.3 | 518.0 |

Example 4—Series (Ig) Compounds

Figure 7:
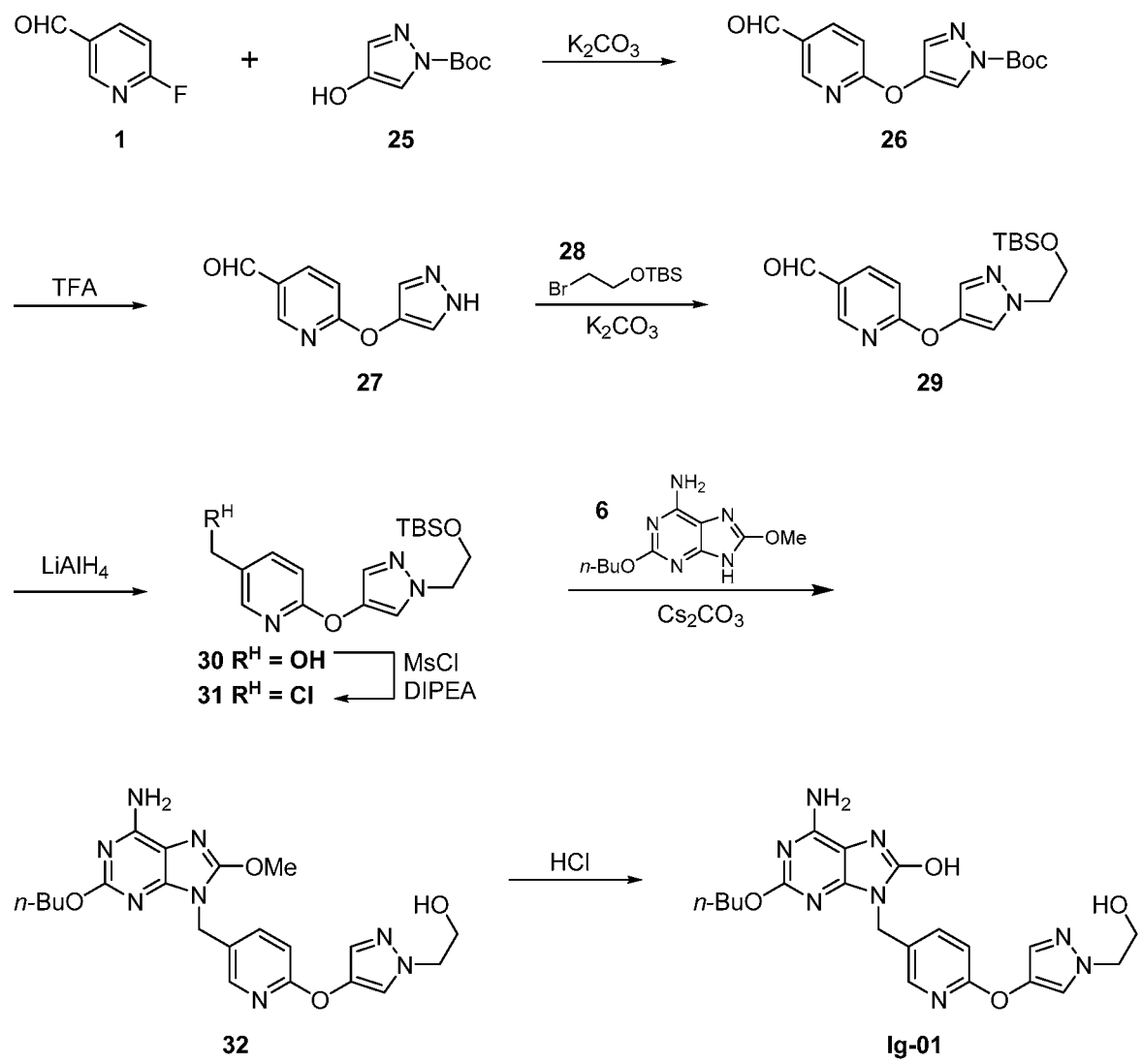

This example and FIG. 7 relate to the preparation of compound Ig-01.

A mixture of compound 25 (CAS Reg. No. 1394947-77-3, 2.36 g, 12.81 mmol) and compound 1 (1.923 g, 15.38 mmol) in DMF (25.6 ml) was treated with K$_2$CO$_3$ (2.125 g, 15.38 mmol) and then stirred at 50° C. overnight. The reaction was quenched with water and stirred for 1 h. The resulting creamy colored solid was collected by filtration and air dried to yield compound 26 (3.51 g, 12.13 mmol, 95% yield). $^1$H NMR (400 MHz, CHLOROFORM-d) δ 10.03 (s, 1H), 8.69 (d, J=2.0 Hz, 1H), 8.36 (d, J=0.7 Hz, 1H), 8.21 (dd, J=8.6, 2.4 Hz, 1H), 7.81 (d, J=0.7 Hz, 1H), 7.09 (d, J=8.8 Hz, 1H), 1.70-1.65 (m, 9H)

To a stirred mixture of compound 26 (1.0 g, 3.46 mmol) in DCM (5 mL) was added TFA (2.66 mL, 34.6 mmol), after stir at RT for 5 h, the reaction mixture was concentrated to dryness. The crude product was then taken in DCM and neutralized carefully with saturated $NaHCO_3$ carefully. The two layers were separated. The aqueous layer was back extracted with DCM (2x). The combined organic extracts were dried over $Na_2SO_4$, filtered and concentrated. The crude product was purified on an ISCO silica column (40 g), eluted with 20% MeOH in DCM (DCM gradient 0-30%). The desired fractions were concentrated to yield compound 27 (490 mg, 2.59 mmol, 74.9% yield). LCMS ESI: calculated for $C_9H8N3O2=190.1$ (M+H$^+$), found 190.1 (M+H$^+$).

A mixture of compound 27 (243 mg, 1.285 mmol) in DMF (5 mL) was treated with $K_2CO_3$ (231 mg, 1.670 mmol), followed by compound 28 (461 mg, 1.927 mmol). The reaction mixture was stirred at 90° C. overnight. The reaction mixture was quenched with water and extracted with ethyl acetate (3×). The combined organic extracts were dried over $Na_2SO_4$, filtered and concentrated. The crude product was purified by ISCO silica column (24 g), eluted with ethyl acetate/hexanes, 0-80% gradient. The desired fractions were concentrated to yield compound 29 (230 mg, 0.662 mmol, 51.5% yield). LCMS ESI: calculated for $C_{17}H_{26}N_3O_3Si=348.2$ (M+H$^+$), found 348.2 (M+H$^+$). $^1$H NMR (400 MHz, CHLOROFORM-d) δ 10.01 (s, 1H), 8.65 (d, J=2.0 Hz, 1H), 8.20-8.16 (m, 1H), 7.79 (s, 1H), 7.61 (s, 1H), 7.06 (d, J=8.6 Hz, 1H), 4.28 (t, J=5.2 Hz, 2H), 3.99 (t, J=5.1 Hz, 2H), 0.87 (s, 6H), 0.00 (d, J=2.9 Hz, 9H).

A solution of compound 29 (100 mg, 0.288 mmol) in MeOH (3 mL) was treated with $NaBH_4$ (10.89 mg, 0.288 mmol) and then stirred at RT for 2 h. The reaction mixture was quenched with water and extracted with ethyl acetate (3×). The combined organic extracts were dried over $Na_2SO_4$, filtered and concentrated. The crude product was purified by ISCO silica column (24 g), eluted with ethyl acetate/hexanes, 0-100% gradient. The desired fractions were concentrated to yield compound 30 (70 mg, 0.200 mmol, 69.6% yield). LCMS ESI: calculated for $C_{17}H_{28}N_3O_3Si=350.2$ (M+H$^+$), found 350.4 (M+H$^+$). 1H NMR (400 MHz, CHLOROFORM-d) δ 8.18 (d, J=1.8 Hz, 1H), 7.74 (dd, J=8.4, 2.4 Hz, 1H), 7.68 (s, 1H), 7.51 (s, 1H), 6.94 (d, J=8.4 Hz, 1H), 4.69 (s, 2H), 4.22 (t, J=5.3 Hz, 2H), 3.98 (t, J=5.3 Hz, 2H), 0.88 (s, 9H), 0.03-0.01 (m, 3H), 0.00 (s, 3H).

Compound 30 (110 mg, 0.315 mmol) in DCM (3 mL) was treated, with stirring, with Hunig's base (0.060 mL, 0.346 mmol), followed by Ms-Cl (0.026 mL, 0.330 mmol) slowly at 0° C., followed by stirring at RT for 14 h. The reaction mixture was quenched with water and extracted with DCM (3x). The combined organic extracts were dried over $Na_2SO_4$, filtered and concentrated to yield compound 31 (110 mg, 0.353 mmol, 94% yield), which was directly carried over to next step without further purification. LCMS ESI: calculated for $C_{17}H_{27Cl}N_3O_2Si=368.1$ (M+H$^+$), found 368.2 (M+H$^+$). $^1$H NMR (400 MHz, CHLOROFORM-d) δ 8.21 (d, J=2.0 Hz, 1H), 7.80 (dd, J=8.6, 2.6 Hz, 1H), 7.74 (s, 1H), 7.63 (s, 1H), 7.00 (d, J=8.4 Hz, 1H), 4.57 (s, 2H), 4.37-4.28 (m, 2H), 4.05 (dd, J=5.5, 4.2 Hz, 2H), 0.92 (s, 9H), 0.10 (s, 6H).

Compound 31 was then taken to compound Ig-01, using the procedures of the preceding examples, mutatis mutandis. LCMS ESI: calculated for $C_{20}H_{25}N_8O_4=441.2$ (M+H$^+$), found 441.0 (M+H$^+$). $^1$H NMR (500 MHz, DMSO-d$_6$) δ 10.10 (s, 1H), 8.15 (d, J=1.8 Hz, 1H), 7.81 (s, 1H), 7.76 (dd, J=8.5, 2.4 Hz, 1H), 7.41 (s, 1H), 6.97 (d, J=8.5 Hz, 1H), 6.48 (br s, 2H), 4.84 (s, 2H), 4.15 (t, J=6.6 Hz, 2H), 4.08 (t, J=5.6 Hz, 2H), 2.91 (br d, J=6.4 Hz, 2H), 1.71-1.54 (m, 2H), 1.46-1.28 (m, 2H), 0.90 (t, J=7.3 Hz, 3H).

Example 5—TLR7 Agonist Activity Assay

This example describes a method for assaying TLR7 agonist activity of the compounds disclosed in this specification.

Engineered human embryonic kidney blue cells (HEK-Blue™ TLR cells; Invivogen) possessing a human TLR7-secreted embryonic alkaline phosphatase (SEAP) reporter transgene were suspended in a non-selective, culture medium (DMEM high-glucose (Invitrogen), supplemented with 10% fetal bovine serum (Sigma)). HEK-Blue™ TLR7 cells were added to each well of a 384-well tissue-culture plate (15,000 cells per well) and incubated 16-18 h at 37° C., 5% $CO_2$. Compounds (100 nl) were dispensed into wells containing the HEK-Blue™ TLR cells and the treated cells were incubated at 37° C., 5% $CO_2$. After 18 h treatment ten microliters of freshly-prepared Quanti-Blue™ reagent (Invivogen) was added to each well, incubated for 30 min (37° C., 5% $CO_2$) and SEAP levels measured using an Envision plate reader (OD=620 nm). The half maximal effective concentration values ($EC_{50}$; compound concentration which induced a response halfway between the assay baseline and maximum) were calculated.

FIG. 6 is a representative graph showing the data so obtained for compound (Ib-02).

Example 6—Interleukin 6 Induction Assay

This example describes a method for assaying interleukin 6 induction by compounds disclosed in this specification.

Compounds diluted in DMSO were transferred to individual wells of a Matrix Tech-nologies clear, V-bottom 384-well plate using ECHO acoustic liquid handling technology (25 nL per well). Human whole-blood samples (25 uL) were added to each well using a CyBio FeliX liquid handling instrument. The plate was shaken on a plate shaker for three min before incubating the reaction mixtures at 37° C. for 20 h. Basel RPMI 1640 medium (supplemented with L-glutamine) was then added to each well (25 uL per well) prior to liberating plasma from each sample by centrifugation (450×g, 5 min, ambient temperature). Treated plasma samples (3 uL) were subsequently transferred to individual wells of a white, shallow, 384-well ProxiPlate (Perkin Elmer) using the FeliX liquid handling instrument and their interleukin 6 levels were measured using AlphaLISA technology as described by the manufacturer, PerkinElmer. Data analyses software was used to determine compound $EC_{50}$ values where the baseline was established using average DMSO values and 100% induction established using reference compound values at the highest concentration tested. $EC_{50}$'s can be determined with software such as Graphpad Prism™.

Example 7—Transglutaminase-Mediated Conjugation

The following procedure can be used for transglutaminase mediated conjugation of agonist-linker compounds wherein the linker has an amine group that can act as an amine donor. The antibody can be one that has a transglutaminase-reactive glutamine, for example one with an N297A or N297Q substitution. Conjugation is carried out by recombinant bacterial transglutaminase with a molar ratio of antibody:enzyme of 5:1. The conjugation is carried out using standard protocols in 50 mM Tris buffer, pH 8.0, incubated overnight at 37° C. The resulting conjugate is purified on a Protein A column, pre-equilibrated with 50 mM Tris, pH 8.0. The conjugate is eluted with 0.1 M sodium citrate buffer, pH 3.5. The eluted fractions are neutralized with 1M Tris pH 9.0. The conjugate can be formulated in 20 mg/mL Sorbitol, 10 mg/mL Glycine, pH 5.0.

Those skilled in the art will understand that the conditions and methodologies in this example are illustrative and non-limiting and that variations thereof or other approaches for conjugation are known in the art and usable in the present invention.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Akinbobuyi et al., ACS 2013 69th Southwest Regional Meeting, Abstract SWRM-70, "Synthesis and evaluation of purine-based toll-like receptor 7 agonists and their antibody conjugates."

Akinbobuyi et al., ACS 2015 Joint Southeastern/Southwest Regional Meeting, Abstract 392, "Synthesis of functionalized purine analogs for antibody conjugation" [2015a].

Akinbobuyi et al., Tetrahedron Lett. 2015, 56, 458, "Facile syntheses of functionalized toll-like receptor 7 agonists" [2015b].

Akinbobuyi et al., Bioorg. Med. Chem. Lett. 2016, 26, 4246, "Synthesis and immunostimulatory activity of substituted TLR7 agonists."

Barberis et al., US 2012/0003298 A1 (2012).

Beesu et al., J. Med. Chem. 2017, 60, 2084, "Identification of High-Potency Human TLR8 and Dual TLR7/TLR8 Agonists in Pyrimidine-2,4-diamines."

Berghöfer et al., J Immunol. 2007, 178, 4072, "Natural and Synthetic TLR7 Ligands Inhibit CpG-A- and CpG-C-Oligodeoxynucleotide-Induced IFN-α Production."

Bonfanti et al., US 2014/0323441 A1 (2015) [2015a].

Bonfanti et al., US 2015/0299221 A1 (2015) [2015b].

Carson et al., US 2013/0202629 A1 (2013).

Carson et al., U.S. Pat. No. 8,729,088 B2 (2014).

Carson et al., U.S. Pat. No. 9,050,376 B2 (2015).

Carson et al., US 2016/0199499 A1 (2016).

Chan et al., Bioconjugate Chem. 2009, 20, 1194, "Synthesis and Immunological Characterization of Toll-Like Receptor 7 Agonistic Conjugates."

Chan et al., Bioconjugate Chem. 2011, 22, 445, "Synthesis and Characterization of PEGylated Toll Like Receptor 7 Ligands."

Cortez et al., US 2017/0044168 A1 (2017). [2017a].

Cortez et al., US 2017/0121421 A1 (2017). [2017b].

Desai et al., U.S. Pat. No. 9,127,006 B2 (2015).

Ding et al., WO 2016/107536 A1 (2016).

Ding et al., US 2017/0273983 A1 (2017) [2017a].

Ding et al., WO 2017/076346 A1 (2017) [2017b].

Gadd et al., Bioconjugate Chem. 2015, 26, 1743, "Targeted Activation of Toll-Like Receptors: Conjugation of a Toll-Like Receptor 7 Agonist to a Monoclonal Antibody Maintains Antigen Binding and Specificity."

Graupe et al., U.S. Pat. No. 8,993,755 B2 (2015).

Halcomb et al., U.S. Pat. No. 9,161,934 B2 (2015).

Hashimoto et al., US 2009/0118263 A1 (2009).

Hirota et al., U.S. Pat. No. 6,028,076 (2000).

Holldack et al., US 2012/0083473 A1 (2012).

Isobe et al., U.S. Pat. No. 6,376,501 B1 (2002).

Isobe et al., JP 2004137157 (2004).

Isobe et al., J. Med. Chem. 2006, 49 (6), 2088, "Synthesis and Biological Evaluation of Novel 9-Substituted-8-Hydroxyadenine Derivatives as Potent Interferon Inducers."

Isobe et al., U.S. Pat. No. 7,521,454 B2 (2009) [2009a].

Isobe et al., US 2009/0105212 A1 (2009) [2009b].

Isobe et al., US 2011/0028715 A1 (2011).

Isobe et al., U.S. Pat. No. 8,148,371 B2 (2012).

Jensen et al., WO 2015/036044 A1 (2015).

Kasibhatla et al., U.S. Pat. No. 7,241,890 B2 (2007).

Koga-Yamakawa et al., Int. J. Cancer 2013, 132 (3), 580, "Intratracheal and oral administration of SM-276001: A selective TLR7 agonist, leads to antitumor efficacy in primary and metastatic models of cancer."

Li et al., U.S. Pat. No. 9,902,730 B2 (2018).

Lioux et al., U.S. Pat. No. 9,295,732 B2 (2016).

Lund et al., Proc. Nat'l Acad. Sci (USA) 2004, 101 (15), 5598, "Recognition of single-stranded RNA viruses by Toll-like receptor 7."

Maj et al., U.S. Pat. No. 9,173,935 B2 (2015).

McGowan et al., J. Med. Chem. 2017, 60, 6137, "Identification and Optimization of Pyrrolo[3,2-d]pyrimidine Toll-like Receptor 7 (TLR7) Selective Agonists for the Treatment of Hepatitis B."

Musmuca et al., J. Chem. Information & Modeling 2009, 49 (7), 1777, "Small-Molecule Interferon Inducers. Toward the Comprehension of the MolecularDeterminants through Ligand-Based Approaches."

Ogita et al., US 2007/0225303 A1 (2007).

Peterson, Rachel; Honor Program Thesis, "Synthesis of Sulfur and Amino-8-Substituted Adenine Derivatives as TLR7 Agonists," Baylor University (2014).

Pryde, U.S. Pat. No. 7,642,350 B2 (2010).

Roethle et al., J. Med. Chem 2013, 56, 7324, "Identification and Optimization of Pteridinone Toll-like Receptor 7 (TLR7) Agonists for the Oral Treatment of Viral Hepatitis."

Seifert, Zacharie; Master of Science Thesis, "Synthesis and Evaluation of 8-Substituted Adenine Derivatives as Toll-like Receptor 7 Agonists," Baylor University (2015).

Vemejoul et al., US 2014/0141033 A1 (2014).

Yu et al., *PLoS One* 2013, 8 (3), e56514, "Toll-Like Receptor 7 Agonists: Chemical Feature Based Pharmacophore Identification and Molecular Docking Studies."

Zhang et al., *Immunity* 2016, 45, 737, "Structural Analysis Reveals that Toll-like Receptor 7 Is a Dual Receptor for Guanosine and Single-Stranded RNA."

Zurawski et al., US 2012/0231023 A1 (2012).

What is claimed is:

1. A compound having a structure according to formula (Ib-12):

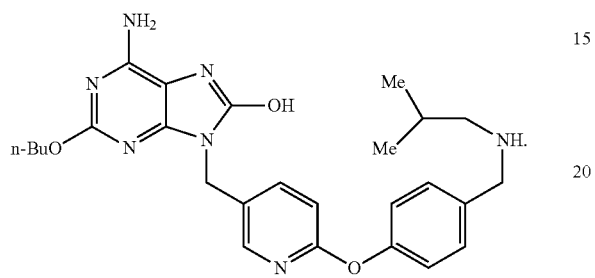

(Ib-12)

* * * * *